US006825034B2

(12) United States Patent
Reeder et al.

(10) Patent No.: US 6,825,034 B2
(45) Date of Patent: Nov. 30, 2004

(54) HUMAN RRN3 AND COMPOSITIONS AND METHODS RELATING THERETO

(75) Inventors: Ronald H. Reeder, Mercer Island, WA (US); Beth Moorefield, Seattle, WA (US); Elizabeth A. Greene, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 09/932,678

(22) Filed: Aug. 16, 2001

(65) Prior Publication Data

US 2002/0090706 A1 Jul. 11, 2002

Related U.S. Application Data

(60) Provisional application No. 60/225,893, filed on Aug. 16, 2000.

(51) Int. Cl.$^7$ .......................... C12N 15/63; C12N 15/11
(52) U.S. Cl. .................................... 435/320.1; 536/23.1
(58) Field of Search ................................. 435/320.1, 41, 435/68.1, 69.1, 69.7, 70.1; 536/23.1, 23.4, 23.5; 530/350, 358

(56) References Cited

U.S. PATENT DOCUMENTS

2002/0146801 A1 * 10/2002 Grummt et al. ............ 435/199

FOREIGN PATENT DOCUMENTS

WO         WO 99/0549      *  2/1999

OTHER PUBLICATIONS

Moorefield et al (Apr. 25, 2000, Proc. Natl. Acad. Sci. USA, vol. 97, pp. 4724–4729).*
Scott et al (Nature Genetics, 1999, 21:440–443).*
Skolnick et al. (2000, Trends in Biotech. 18:34–39).*
Bork (2000, Genome Research 10:398–400).*
Doerks et al. (1998, Trends in Genetics 14:248–250).*
Smith et al. (1997, Nature Biotechnology 15:1222–1223).*
Brenner (1999, Trends in Genetics 15:132–133).*
Bork et al. (1996, Trends in Genetics 12:425–427).*
Bowie et al. (1990, Science 247:1306–1310).*
Kunkel, "Rapid and Efficient Site–Specific Mutagenesis Without Phenotypic Selection," *Proc. Natl. Acad. Sci. USA*, 82:488–92 (Jan., 1985).
Grussenmeyer et al., "Complexes of Polyoma Virus Medium T Antigen and Cellular Proteins," *Proc. Natl. Acad. Sci. USA*, 82:7952–54 (Dec., 1985).
Bell et al., "Functional Cooperativity Between Transcription Factors UBF1 and SL1 Mediates Human Ribosomal RNA Synthesis," *Science*, 241:1192–97 (Sep. 2, 1988).
Schnapp et al., "A Growth–Dependent Transcription Initiation Factor (TIF–IA) Interacting with RNA Polymerase I Regulates Mouse Ribosomal RNA Synthesis," *EMBO J.*, 9:2857–63 (1990).

Nogi et al., "An Approach for Isolation of Mutants Defective in 35S Ribosomal RNA Synthesis in *Saccharomyces Cerevisiae*." *Proc. Natl. Acad. Sci. USA*. 88:7026–30 (Aug., 1991).
Schnapp and Grummt, "Transcription Complex Formation at the Mouse rDNA Promoter Involves the Stepwise Association of Four Transcription Factors and RNA Polymerase I," *J. Biol. Chem.*, 266:24588–95 (Dec. 25, 1991).
Comai et al., "The TATA–Binding Protein and Associated Factors Are Integral Components of the RNA Polymerase I Transcription Factor, SL 1," *Cell*, 68:965–76 (Mar. 6, 1992).
Eberhard et al., "A TBP–Containing Multiprotein Complex (TIF–IB) Mediates Transcription Specificity of Murine RNA Polymerase I," *Nucleic Acids Res.*, 21:4180–86 (Aug. 2, 1993).
Schnapp et al., "Function of the Growth–Regulated Transcription Initiation Factor TIF–IA in Initiation Complex Formation at the Murine Ribosomal Gene Promoter," *Mol. Cell. Biol.*, 13:6723–32 (1993).
Keys et al., "RRN6 and RRN7 Encode Subunits of a Multiprotein Complex Essential for the Initiation of rDNA Transcription by RNA Polymerase I in *Saccharomyces Cerevisiae*," *Genes Dev.*, 8:2349–62 (1994).
Schnapp et al., "TIF–IC, a Factor Involved in Both Transcription Initiation and Elongation of RNA Polymerase I," *EMBO J.*, 13:4028–35 (1994).
Keys et al., "Multiprotein Transcription Factor UAF Interacts with the Upstream Element of the Yeast RNA Polymerase I Promoter and Forms a Stable Preinitiation Complex," *Genes Dev.*, 10:887–903 (Feb. 27, 1996).
Lalo et al., "RRN11 Encodes the Third Subunit of the Complex Containing Rrn6p and Rrn7p That Is Essential for the Initiation of rDNA Transcription by Yeast RNA Polymerase I," *J. Biol. Chem.*, 271:21062–67 (Aug. 30, 1996).
Lin et al., "A Novel 66–Kilodalton Protein Complexes with Rrn6, Rrn7, and TATA–Binding Protein To Promote Polymerase 1 Transcription Initiation in *Saccharomyces Cerevisiae*," *Mol. Cell. Biol.*, 16:6436–43 (Nov., 1996).
Steffan et al., "The Role of TBP in rDNA Transcription by RNA Polymerase I in *Saccharomyces Cerevisiae* TBP is required for Upstream Activation Factor–Dependent Recruitment of Core Factor," *Genes Dev.*, 10:2551–63 (1996).

(List continued on next page.)

Primary Examiner—Larry R. Helms
Assistant Examiner—Misook Yu
(74) Attorney, Agent, or Firm—Townsend and Townsend and Crew LLP

(57) ABSTRACT

Polynucleotide sequences encoding eukaryotic Rrn3 polypeptides are provided. Rrn3 is a eukaryotic RNA polymerase I transcription factor. The Rrn3 polypeptides, and antibodies thereto, can be used as diagnostic tools, as therapeutic agents and to identify agonist and antagonists of Rrn3.

5 Claims, No Drawings

OTHER PUBLICATIONS

Yamamoto et al., "RRN3 Gene of *Saccharomyces Cerevisiae* Encodes an Essential RNA Polymerase I Transcription Factor Which Interacts with the Polymerase Independently of DNA Template," *EMBO J.*, 15:3964–73 (1996).

Heix et al., "Cloning of Murine RNA Polymerase I–Specific TAF Factors: Conserved Interactions Between the Subunits of the Species–Specific Transcription Initiation Factor TIF–IB/SL 1," *Proc. Natl. Acad. Sci. USA*, 94:1733–38 (Mar., 1997).

Keener et al., "Reconstitution of Yeast RNA Polymerase I Transcription in Vitro from Purified Components," *J. Biol. Chem.*, 273:33795–802 (Dec. 11, 1998).

Milkereit and Tschochner, "A Specialized Form of RNA Polymerase I, Essential for Initiation and Growth–Dependent Regulation of rRNA Synthesis, is Disrupted During Transcription," *EMBO J.*, 17:3692–703 (1998).

Steffan et al., "Interaction of TATA–Binding Protein with Upstream Activation Factor Is Required for Activated Transcription of Ribosomal DNA by RNA Polymerase I in *Saccharomyces Cerevisiae* In Vivo," *Mol. Cell. Biol.*, 18:3752–61 (Jul., 1998).

* cited by examiner

HUMAN RRN3 AND COMPOSITIONS AND METHODS RELATING THERETO

CROSS-REFERENCES TO RELATED APPLICATIONS

This application claims priority from Provisional Application U.S. Ser. No. 60/225,893, filed Aug. 16, 2000, the disclosure of which is incorporated herein by reference.

STATEMENT AS TO RIGHTS TO INVENTIONS MADE UNDER FEDERALLY SPONSORED RESEARCH AND DEVELOPMENT

This work was supported by grants GM26624 and CA09657 from the National Institutes of Health. The U.S. government may have certain rights in the invention pursuant to a grant received from the U.S. National Institutes of Health.

BACKGROUND OF THE INVENTION

The ribosomal RNA genes ("rRNA") of eukaryotic cells are transcribed by an enzyme solely dedicated to that purpose, RNA polymerase I ("pol I"). The expression of the rRNA genes is coordinated with cellular proliferation. When cell growth is impaired by nutrient deprivation or depletion, transcription of the rRNA genes declines: This decline is reversed when growth-permissive conditions are restored. Since growth-rate dependence is a universal feature of rRNA gene regulation, identifying the molecular mechanisms that couple pol I activity to cell growth is a central question in studies of all eukaryotic systems, including the yeast and mammalian systems.

Transcription of rRNA genes of the yeast *Saccharomyces cerevisiae* requires the activity of at least three transcription factors, which have been defined both genetically and biochemically. Two of these factors, Core Factor and Upstream Activation Factor, are multi-subunit factors that interact directly with distinct elements of the rRNA promoter to assemble a preinitiation complex. Core Factor ("CF") is composed of three essential gene products, Rrn6, Rrn7, and Rrn11, and associates with TATA box binding protein ("TBP"). CF is required to direct transcription initiation from the core promoter of an rRNA gene both in vitro and in vivo (see Keys et al., *Genes Dev.* 8:2349–62 (1994); Lin et al., *Mol. Cell. Biol.* 16:6436–43 (1996); Steffan et al., *Genes Dev.* 10:2551–63 (1996); Keener et al., *J. Biol. Chem.* 273:33795–802 (1998); Lalo et al., *J. Biol. Chem.* 271:21062–67 (1996)). Upstream Activation Factor ("UAF") binds to the upstream promoter element and stimulates transcription from the core promoter. When the yeast genes encoding the UAF subunits Rrn5, Rrn9, or Rrn10 are individually disrupted, cells remain viable but exhibit pronounced growth defects, indicating that UAF activity is necessary to support levels of rRNA synthesis required for normal cell growth (see Keys et al., *Genes Dev.* 10:887–903 (1996)). UAF subunits interact with CF subunits in vitro, and direct interaction of UAF with TBP has been shown to mediate transcriptional activation in vivo (see Steffan et al. (1996), supra; Steffan et al., *Mol. Cell. Biol.* 18:3752–61 (1998)).

A third transcription factor, Rrn3, is unique in that it functions as a single subunit, shows no sequence-specific DNA binding activity, and is not required for pre-initiation complex assembly (see Yamamoto et al., *EMBO J.* 15:3964–73 (1996)). The Rrn3 protein appears instead to function by direct interaction with RNA polymerase I since it is stably associated with pol I in transcriptionally active extracts (see Milkereit and Tschochner, *EMBO J.* 17:3692–703 (1998)). The transcriptional activity of pol I is enhanced by pre-incubation with Rrn3 protein in the absence of either DNA template or other pol I transcription factors (see Yamamoto et al. (1996), supra; Keener et al. (1998), supra). The interaction of Rrn3 polypeptide with RNA polymerase I fluctuates with changes in cellular growth rate; Rrn3 polypeptide is not associated with pol I in transcriptionally-inactive extracts prepared from growth-arrested cells. Transcriptional activity is restored upon addition of Rrn3-associated pol I purified from growing cells (see Milkereit and Tschochner, supra). These observations suggest that Rrn3 activity may be regulated in a growth-dependent manner. Although the specific function of Rrn3 polypeptide is as yet unknown, it is essential for rRNA gene transcription in vivo and in vitro, and it may be required to mediate productive interactions of pol I with the pre-initiation complex.

Transcription of mammalian rRNA genes also requires two promoter-binding transcription factors which appear to perform functions similar to those of the yeast pol I factors. The mammalian transcription factors are not conserved with those of yeast. The core promoter-binding factor IF-IB/SL1, which is essential for transcription, is comprised of TBP and three transcription-associated factors ("TAF's"). The TAF's are similar in size to the three yeast CF subunits, but display no amino acid sequence similarity to their yeast counterparts (see Comai et al., *Cell* 68:965–76 (1992); Eberhard et al., *Nucleic Acids Res.* 21:4180–86 (1993); Heix et al., *Proc. Natl. Acad. Sci. USA* 94:1733–38 (1997)). The upstream stimulatory activity in mammalian cells is mediated by a single protein, UBF, which bears no resemblance to the multi-subunit yeast UAF complex (see Bell et al., *Science* 241:1192–97 (1988); Schnapp and Grummt, *J. Biol. Chem.* 266:24588–95 (1991)). DNA binding by UBF is mediated by high mobility group domains which are not present in any of the yeast pol I transcription factors, and no proteins related to the yeast UAF subunits have been identified in mammals to date. It therefore appears that the promoter-binding factors of yeast and mammals are evolutionarily divergent.

In mammalian cells, two RNA polymerase I-associated factors, TIF-IA and TIF-IC, have been identified (see Schnapp et al., *EMBO J.* 9:2857–63 (1990); Schnapp et al., *EMBO J.* 13:4028–35 (1994)). Like yeast Rrn3 ("yRrn3"), TIF-IA and TIF-IC are not required for pre-initiation complex assembly but are essential for transcription initiation by pol I (see Schnapp and Grummt, supra). The relationship of these factors to yRrn3 has not yet been determined since their genes have not yet been isolated. However, TIF-IA shares an important functional similarity with yRrn3 in that its activity is regulated by cellular growth rate (see Schnapp et al. (1990), supra; Schnapp et al., *Mol Cell. Biol.* 13:6723–32 (1993)).

rRNA synthesis is required for cell division and differentiation, and also for normal cellular metabolism. The assembly of new ribosomal subunits requires new rRNA transcripts. Thus, rRNA transcription provides a common regulatory point for controlling cell proliferation in a wide variety of cell types. Reagents that modulate rRNA transcription could be used to affect proliferation in such a wide variety of cell types, and would not be limited to current reagents that are cell-type specific. For example, reagents, and methods of their use, that modulate rRNA synthesis could be used to stimulate hypoproliferative cells or to inhibit hyperproliferative cells, in diseases such as cancer.

There is need, therefore, for reagents, and methods of using such reagents, to modulate cell proliferation through rRNA transcription. Surprisingly, the present invention fulfills these and other related needs.

SUMMARY OF THE INVENTION

The present invention relates to the discovery, identification and characterization of eukaryotic RRN3 genes. The invention encompasses nucleotide sequences of the RRN3 gene and amino acid sequences of its encoded polypeptide product, as well as fragments, derivatives and analogs thereof. The invention also encompasses the production of Rrn3 polypeptides and antigen-specific antibodies. The invention further encompasses compositions and methods for screening, diagnostic and therapeutic applications.

One aspect relates to RRN3 nucleic acids, including mRNAs, DNAs, cDNAs, genomic DNA, as well as RRN3 antisense nucleic acids. Such nucleic acids include the RRN3 cDNA having the nucleotide sequence of SEQ ID NO:1. Another aspect relates to RRN3 nucleic acid derivatives or fragments that encode Rrn3 polypeptides, or portions thereof. Such derivatives include nucleic acids encoding all possible codon choices for the same amino acid or conservative amino acid substitutions thereof. Other RRN3 nucleic acids include those nucleic acids that are capable of selectively hybridizing to a human RRN3 cDNA (e.g., SEQ ID NO:1) under stringent hybridization conditions. A related aspect of the present invention relates to nucleic acid probes comprising polynucleotides of sufficient length to selectively hybridize to a polynucleotide encoding an Rrn3 polypeptide of the present invention.

In another aspect, the present invention provides substantially pure preparations of human Rrn3 and polypeptide fragments, derivatives and analogs thereof. In a related aspect, the invention concerns nucleic acid constructs for expressing the RRN3 nucleic acids. Such expression constructs typically comprise a transcriptional promoter, a nucleic acid which encodes the Rrn3 polypeptide, derivative or fragment thereof, and a transcriptional terminator, each operably linked for expression of the Rrn3 polypeptide, derivative or fragment. In another aspect, the invention provides the ability to produce Rrn3 polypeptides, derivatives, or fragments thereof by recombinant means, typically in cultured eukaryotic cells or in prokaryotic cells. The expressed Rrn3 polypeptide, derivatives or fragments can have the same functional activity as the corresponding native Rrn3 polypeptide, or an altered activity. Accordingly, isolated and purified polynucleotides are described which encode Rrn3 polypeptide, derivatives, and fragments thereof, where the polynucleotides can be in the form of RRN3 nucleic acids, such as genomic DNA, cDNA, or mRNA.

In another aspect, the RRN3 nucleic acids can be used to identify other mammalian genes that encode Rrn3-like molecules. The RRN3 nucleic acids can also be used to screen for mutations in a RRN3 gene that are associated with certain diseases. As such, the invention further relates to materials and methods for the identification of disease-associated mutations, where the RRN3 nucleic acids are used to detect the presence of mutations in a biological sample. RRN3 nucleic acid probes can also be used to identify mutations in a RRN3 gene for diagnostic purposes. The probes can be full-length genomic DNA, cDNA, RNA or nucleic acids as small as from about 14 to 25 nucleotides, more often though from about 40 to about 50, or more nucleotides in length.

The invention also provides antibodies to Rrn3 polypeptide, in the form of polyclonal or monoclonal antibodies. Such antibodies can specifically bind to an Rrn3 polypeptide or fragment, derivative or analog thereof, and can be incubated with a biological sample under conditions conducive to immune complex formation, such as by ELISA. The resulting complexes can then be detected, typically by means of a label such as an enzyme, fluorophore, radionuclide, chemiluminescent, particle, or a second labeled antibody. Thus, means are provided for immunohistochemical staining of tissues, including tumor biopsies. The invention further relates to methods of identifying agonists and antagonists that modulate the activity of an Rrn3 polypeptide, and further provides a method for identifying agents that specifically affect one Rrn3 polypeptide, without affecting other Rrn3 polypeptides.

A further understanding of the nature and advantages on the invention will become apparent by reference to the remaining portions of the specification.

DESCRIPTION OF THE SPECIFIC EMBODIMENTS

Prior to setting forth the invention in more detail, it may be helpful to a further understanding thereof to set forth definitions of certain terms as used hereinafter.

Definitions

Unless defined otherwise, all technical and scientific terms used herein have the same meaning as commonly understood by one of ordinary skill in the art to which this invention belongs. Although any methods and materials similar to those described herein can be used in the practice or testing of the present invention, only exemplary methods and materials are described. For purposes of the present invention, the following terms are defined below.

The term "RRN3 locus" and "RRN3 gene" refer to the coding sequences, intervening sequences and regulatory elements controlling transcription and/or translation. The terms "RRN3 locus" and "RRN3 gene" include all allelic variations of RRN3. A wild-type RRN3 sequence refers to the sequence of SEQ ID NO:1.

The term "RRN3 nucleic acids" refers to polynucleotides from the RRN3 locus, such as those encoding Rrn3 polypeptides, including mRNAs, DNAs, cDNAs, genomic DNA, as well as antisense nucleic acids, and polynucleotides encoding fragments, derivatives and analogs thereof. Useful fragments and derivatives include those based on all possible codon choices for the same amino acid, and codon choices based on conservative amino acid substitutions. Useful derivatives further include those having at least 50% or at least 70% polynucleotide sequence identity, and typically 80%, more typically 90% sequence identity, to the RRN3 nucleic acid of SEQ ID NO:1.

The terms "polynucleotide" and "nucleic acid" refer to a polymer composed of a multiplicity of nucleotide units (ribonucleotide or deoxyribonucleotide or related structural variants) linked via phosphodiester bonds. A polynucleotide or nucleic acid can be of substantially any length, typically from about six (6) nucleotides to about $10^9$ nucleotides or larger. Polynucleotides and nucleic acids include RNA, cDNA, genomic DNA, synthetic forms, and mixed polymers, both sense and antisense strands, and can also be chemically or biochemically modified or can contain non-natural or derivatized nucleotide bases, as will be readily appreciated by the skilled artisan. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "oligonucleotide" refers to a polynucleotide of from about six (6) to about one hundred (100) nucleotides or more in length. Thus, oligonucleotides are a subset of polynucleotides. Oligonucleotides can be synthesized on an automated oligonucleotide synthesizer (for example, those manufactured by Applied BioSystems (Foster City, Calif.)) according to specifications provided by the manufacturer.

The term "primer" as used herein refers to a polynucleotide, typically an oligonucleotide, whether occurring naturally, as in an enzyme digest, or whether produced synthetically, which acts as a point of initiation of polynucleotide synthesis when used under conditions in which a primer extension product is synthesized. A primer can be single-stranded or double-stranded.

"Rrn3 polypeptide" refers to a polypeptide encoded by the RRN3 locus, and fragments, derivatives or analogs thereof. The term "polypeptide" refers to a polymer of amino acids and its equivalent and does not refer to a specific length of the product; thus, peptides, oligopeptides and proteins are included within the definition of a polypeptide. A "fragment" refers to a portion of a polypeptide typically having at least 10 contiguous amino acids, more typically at least 20, still more typically at least 50 contiguous amino acids of the Rrn3 polypeptide. A derivative is a polypeptide having conservative amino acid substitutions, as compared with another sequence. Derivatives further include, for example, glycosylations, acetylations, phosphorylations, and the like. Further included within the definition of "polypeptide" are, for example, polypeptides containing one or more analogs of an amino acid (e.g., unnatural amino acids, and the like), polypeptides with substituted linkages as well as other modifications known in the art, both naturally and non-naturally occurring. Ordinarily, such polypeptides will be at least about 50% identical to the native Rrn3 amino acid sequence, typically in excess of about 90%, and more typically at least about 95% identical.

The terms "amino acid" or "amino acid residue", as used herein, refer to naturally occurring L amino acids or to D amino acids as described further below. The commonly used one- and three-letter abbreviations for amino acids are used herein (see, e.g., Alberts et al., *Molecular Biology of the Cell*, 3d ed., Garland Publishing, Inc., New York (1994)).

The term "heterologous" refers to a nucleic acid or polypeptide from a different source, (e.g. a tissue, organism or species), as compared with another nucleic acid or polypeptide.

The term "isolated" refers to a nucleic acid or polypeptide that has been removed from its natural cellular environment. An isolated nucleic acid is typically at least partially purified from other cellular nucleic acids, polypeptides and other constituents.

The term "functionally active" Rrn3 polypeptides refers to those fragments, derivatives and analogs displaying one or more known functional activities associated with a full-length (wild-type) Rrn3 polypeptide (e.g., stimulating rRNA transcription (i.e. synthesis), binding to RNA polymerase I, or other Rrn3 binding partner), antigenicity (binding to an anti-Rrn3 antibody), immunogenicity, and the like. Functionally active molecules include Rrn3 polypeptides, fragments, derivatives and analogs thereof, nucleic acids encoding Rrn3 polypeptides, fragments, and derivatives thereof, and anti-Rrn3 antibodies.

The term "therapeutically effective" refers to an amount of a molecule (e.g., an Rrn3 polypeptide, anti-Rrn3 antibody, or RRN3 nucleic acid) that is sufficient to modulate rRNA transcription in a subject, such as a patient or a mammal.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence, as measured using one of the following sequence comparison algorithms, or by visual inspection.

The phrase "substantially identical," in the context of two nucleic acids or polypeptides, refers to two or more sequences or subsequences that have at least 60%, typically 80%, most typically 90–95% nucleotide or amino acid residue identity, when compared and aligned for maximum correspondence, as measured using one of the following sequence comparison algorithms, or by visual inspection. An indication that two polypeptide sequences are "substantially identical" is that one polypeptide is immunologically reactive with antibodies raised against the second polypeptide.

"Similarity" or "percent similarity" in the context of two or polypeptide sequences, refer to two or more sequences or subsequences that are the same or have a specified percentage of amino acid residues or conservative substitutions thereof, that are the same, when compared and aligned for maximum correspondence, as measured using one of the following sequence comparison algorithms, or by visual inspection. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art, as discussed below.

The term "substantial similarity" in the context of polypeptide sequences, indicates that the polypeptide comprises a sequence with at least 70% sequence identity to a reference sequence, or preferably 80%, or more preferably 85% sequence identity to the reference sequence, or most preferably 90% identity over a comparison window of about 10–20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions.

The term "conservative substitution," when describing a polypeptide, refers to a change in the amino acid composition of the polypeptide that does not substantially alter the polypeptide's activity. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, *Proteins*, W. H. Freeman and Company (1984).) In addition, individual substitutions, deletions or additions that alter, add or delete a single amino acid or a small percentage of amino acids in an encoded sequence are also "conservative substitutions."

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (*Adv. Appl. Math.* 2:482 (1981), which is incorporated by reference herein), by the homology alignment algorithm of Needleman and Wunsch (*J. Mol. Biol.* 48:443–53 (1970), which is incorporated by reference herein), by the search for similarity method of Pearson and Lipman (*Proc. Natl. Acad. Sci. USA* 85:2444–48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), *Current Protocols in Molecular Biology*, 4$^{th}$ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (*J. Mol. Evol.* 25:351–60 (1987), which is incorporated by reference herein). The method used is similar to the method described by Higgins and Sharp (*Comput. Appl. Biosci.* 5:151–53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (*J. Mol. Biol.* 215:403–410 (1990), which is incorporated by reference herein). (See also Zhang et al., *Nucleic Acid Res.* 26:3986–90 (1998); Altschul et al., *Nucleic Acid Res.* 25:3389–402 (1997), which are incorporated by reference herein). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, *Proc. Natl. Acad. Sci. USA* 89:10915–9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, *Proc. Natl. Acad. Sci. USA* 90:5873–77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions.

The term "immunologically cross-reactive" means that a polypeptide, fragment, derivative or analog is capable of competitively inhibiting the binding of an antibody to its antigen.

The terms "transformation" or "transfection" refer to the process of stably altering the genotype of a recipient cell or microorganism by the introduction of polynucleotides. This is typically detected by a change in the phenotype of the recipient cell or organism. The term "transformation" is generally applied to microorganisms, while "transfection" is used to describe this process in cells derived from multicellular organisms.

The term "sample" generally indicates a specimen of tissue, cells, plasma, serum, spinal fluid, lymph fluid, the external sections of the skin, respiratory, intestinal, and genitourinary tracts, tears, saliva, blood cells, hair, tumors, organs, other material of biological origin that contains polynucleotides, or in vitro cell culture constituents of any of these. A sample can further be semi-purified or purified forms of polynucleotides. A sample can be isolated from a mammal, such as a human, an animal, or any other organism having a RRN3 locus, as well as in vitro culture constituents of any of these.

The term "proliferation" refers to activities such as transformation, a change in gene expression, and other changes in cell state that are dependent, directly or indirectly, on new ribosomal RNA synthesis, new ribosome assembly, or new protein synthesis requiring new ribosome assembly. "Hyperproliferation" refers to an increase in one or more proliferative activities, as compared with normal tissue. "Hypoproliferation" refers to an decrease in one or more proliferative activities, as compared with normal tissue.

The term "disease" refers to a disease, condition, or disorder associated with hyperproliferation or hypoproliferation. Diseases involving hyperproliferation include, but are not limited to, cancer, malignancies, premalignant conditions (e.g., hyperplasia, metaplasia, dysplasia), benign tumors, hyperproliferative disorders, benign dysproliferative disorders, autoimmune diseases, and the like. Diseases involving cell hypoproliferation include, but are not limited to, cardiac disease and other conditions in which an increase in cell proliferation is desired.

Generally, other nomenclature used herein and many of the laboratory procedures in cell culture, molecular genetics and nucleic acid chemistry and hybridization, which are described below, are those well known and commonly employed in the art. (See generally Ausubel et al. (1999) supra; Sambrook et al., *Molecular Cloning: A Laboratory Manual*, 3d Ed., Cold Spring Harbor Laboratory Press, New York (2001), which are incorporated by reference herein). Standard techniques are used for recombinant nucleic acid methods, polynucleotide synthesis, preparation of biological samples, preparation of cDNA fragments, isolation of mRNA and the like. Generally enzymatic reactions and purification steps are performed according to the manufacturers' specifications.

Genetic methods suitable for manipulating yeast strains are generally described in Sherman et al., *Methods in Yeast Genetics: A Laboratory Manual* (Cold Spring Harbor, N.Y. (1983)) and "Guide to Yeast Genetics and Molecular Biology" In *Methods in Enzymology* (Guthrie and Fink (eds.), Academic Press, San Diego, Calif. (1991), which are incorporated by reference herein).

The RRN3 Gene

The invention relates to the nucleotide sequences of human RRN3. The human RRN3 cDNA (SEQ ID NO:1) was isolated by a BLAST search using the yeast Rrn3 amino acid sequence as a reference to identify expressed sequence tags ("EST's") corresponding to the human RRN3 gene. The RRN3 cDNA sequence was assembled from the EST's identified by database searching. The RRN3 cDNA encodes a polypeptide of 651 amino acids (SEQ ID NO:2). Analysis of the corresponding polypeptide revealed that it has an apparent molecular weight of about 74 kD, as determined by SDS PAGE, which is consistent with the predicted molecular weight. The human Rrn3 polypeptide is 21% identical and 43% similar to yeast Rrn3 polypeptide. Amino acid conservation is distributed throughout the length of the two polypeptides. Database searching reveals that the human RRN3 cDNA is located on chromosome 16 in a region of greater than 26 kb in length and which contains at least fifteen introns. Expressed sequence tags arising from the RRN3 gene have been isolated from a variety of tissues, including lung, retina, thymus, and prostate. Ubiquitous expression of Rrn3 polypeptide is consistent with its role as a pol I transcription factor for rRNA synthesis.

Three regions of Rrn3 polypeptides are shared by all Rrn3 family members, but are not found in other proteins. These regions are conserved in both sequence and length and display the general consensus sequences:
(1) Tyr(Ile/Leu)(Ala/Gly)(Ala/Ser)(Phe/Tyr)(Ile/Leu) (Ala/Ser)ArgAlaLys;
(2) PheTyr(Ala/Ser)XaaXaaGln(Ala/Ser)(Ile/Leu) XaaXaaXaa (Phe)XaaPheArg; and
(3) PhePro(Phe/Tyr)AspXaaXaaXaaLeu(Lys);
where parentheses indicate positions which vary among family members, and Xaa indicates variable positions. As these motifs are not found in the sequences of other polypeptides, their evolutionary conservation reflects the pol I-specific function of Rrn3 polypeptides. Since yeast Rrn3 polypeptide does not bind to DNA, these regions are likely to mediate protein-protein interactions with other components of the pol I transcriptional machinery.

In a specific embodiment, RRN3 nucleic acids comprise the cDNA sequence of SEQ ID NO:1, or the coding region of the RRN3 locus, or nucleic acid sequences (e.g., an open reading frame) encoding a Rrn3 polypeptide (SEQ ID NO:2). RRN3 nucleic acids further include mRNAs, genomic DNA, and antisense nucleic acids corresponding to the RRN3 locus. RRN3 nucleic acids further include derivatives (e.g., nucleotide sequence variants), such as those encoding other possible codon choices for the same amino acid or conservative amino acid substitutions thereof, such as naturally occurring allelic variants. Due to the degeneracy of nucleotide coding sequences, other DNA sequences which encode substantially the same amino acid sequence as a RRN3 gene, for example, SEQ ID NO:1, can be used in the practice of the present invention. These include, but are not limited to, nucleotide sequences comprising all or portions of a RRN3 gene which is altered by the substitution of different codons that encode the same or a functionally equivalent amino acid residue (e.g., a conservative substitution) within the sequence, thus producing a silent change.

The invention also provides RRN3 nucleic acid fragments of at least 6 contiguous nucleotides (e.g., a hybridizable portion); in other embodiments, the nucleic acids comprise at least 8 contiguous nueleotides, 25 nucleotides, 50 nucleotides, 100 nucleotides, 150 nucleotides, 200 nucleotides, or even up to 250 nucleotides or more of a RRN3 sequence. In another embodiment, the nucleic acids are smaller than 200 or 250 nucleotides in length. The RRN3 nucleic acids can be single or double-stranded. As is readily apparent, as used herein, a "nucleic acid encoding a fragment of an Rrn3 polypeptide" is construed as referring to a nucleic acid encoding only the recited fragment or portion of the Rrn3 polypeptide and not the other contiguous portions of the Rrn3 polypeptide as a contiguous sequence. Fragments of RRN3 nucleic acids encoding one or more Rrn3 domains are also provided.

RRN3 nucleic acids further include those nucleic acids hybridizable to, or complementary to, the foregoing sequences. In specific aspects, nucleic acids are provided which comprise a sequence complementary to at least 10, 25, 50, 100, 200, or 250 nucleotides or more of a RRN3 gene. In a specific embodiment, a nucleic acid which is hybridizable to a RRN3 nucleic acid (e.g., having sequence SEQ ID NO:1), or to a nucleic acid encoding a RRN3 derivative, under conditions of low, medium or high stringency, is provided.

By way of example, and not limitation, procedures using low stringency conditions are as follows: Filters containing DNA are pretreated for 6 hours at 40° C. in a solution containing 35% formamide, 5×SSC, 50 mM Tris-HCl (pH 7.5), 5 mM EDTA, 0.1% polyvinylpyrrolidone (PVP), 0.1% Ficoll, 1% bovine serum albumin (BSA), and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×$10^6$ cpm $^{32}$P-labeled probe. Filters are incubated in hybridization mixture for 18–20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65–68° C. and re-exposed to film. Other conditions of low stringency that can be used are well known in the art (e.g., those employed for cross-species hybridizations). (See also Shilo and Weinberg, *Proc. Natl. Acad. Sci. USA* 78:6789–92 (1981)).

In another embodiment, a nucleic acid which is hybridizable to a RRN3 nucleic acid under conditions of high stringency is provided. By way of example, and not limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5–20×$10^6$ cpm of $^{32}$P-labeled probe. Washing of filters is done at 65° C. for 1 hour in a solution containing 2×SSC, 0.01% PVP, 0.01% Ficoll, and 0.01% BSA. This is followed by a wash in 0.1×SSC at 50° C. for 45 min before autoradiography. Other conditions of high stringency which can be used are well known in the art. (See generally Ausubel et al., supra; Sambrook et al., supra).

In another specific embodiment, a nucleic acid which is hybridizable to a RRN3 nucleic acid under conditions of moderate stringency is provided. By way of example, and not limitation, procedures using such conditions of moderate stringency are as follows: Prehybridization of filters containing DNA is carried out for 8 hours to overnight at 55° C. in buffer composed of 6×SSC, 50 mM Tris-HCl (pH 7.5), 1 mM EDTA, 0.02% PVP, 0.2% Ficoll, 0.02% BSA and 500 µg/ml denatured salmon sperm DNA. Filters are hybridized for 24 hours at 55° C. in a prehybridization mixture containing 100 µg/ml denatured salmon sperm DNA and 5–20× $10^6$ cpm of $^{32}$P-labeled probe. Washing of filters is done at 37° C. for 1 hour in a solution containing 2×SSC, 0.01% PVP, 0.01% Ficoll, and 0.01% BSA.

Various other stringency conditions which promote hybridization can be used. For example, hybridization in 6×SSC at about 45° C., followed by washing in 2×SSC at 50° C. can be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaH$_2$PO4 (pH7.2)/1 mM EDTA/7% SDS, or hybridization in 50% formamide/0.25M NaH$_2$PO$_4$ (pH 7.2)/0.25 M NaCl/1 mM EDTA/7% SDS, followed by washing in 40 mM NaH$_2$PO$_4$ (pH 7.2)/1 mM EDTA/5% SDS at 50° C. or in 40 mM NaH$_2$PO$_4$ (pH7.2)/1 mM EDTA/1% SDS at 50° C. Both temperature and salt can be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al. (supra); and Ausubel et al. (supra).

RRN3 nucleic acids further include derivatives and analogs. Such derivatives and analogs can comprise at least one modified base moiety, such as, for example, 5-fluorouracil, 5-bromouracil, 5-chlorouracil, 5-iodouracil, hypoxanthine, xanthine, 4-acetylcytosine, 5-(carboxy-hydroxylmethyl) uracil, 5-carboxymethylaminomethyl-2-thiouridine, 5-carboxymethylamino-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, 2,6-diaminopurine, and the like. The RRN3 nucleic acids can also have at least one modified sugar moiety, such as, for example, arabinose, 2-fluoroarabinose, xylulose, and hexose.

The RRN3 nucleic acids can also have a modified phosphate backbone, such as, for example, a phosphorothioate, a phosphorodithioate, a phosphoramidothioate, a phosphoramidate, a phosphordiamidate, a methylphosphonate, an alkyl phosphotriester, and a formacetal or analog thereof.

The RRN3 nucleic acids can also be an (α-anomeric oligonucleotide. An α-anomeric oligonucleotide forms specific double-stranded hybrids with complementary RNA in which, contrary to the usual β-units, the strands run parallel to each other (see, e.g., Gautier et al., *Nucl. Acids Res.* 15:6625–41 (1987)).

RRN3 nucleic acid derivatives or analogs can be synthesized by standard methods known in the art (e.g., by use of a commercially available automated DNA synthesizer). As examples, phosphorothioate nucleic acids can be synthesized by the method of Stein et al. (*Nucl. Acids Res.* 16:3209–21 (1988)), and methyphosphonate nucleic acids oligonucleotides can be prepared by use of controlled pore glass polymer supports (Sarin et al., *Proc. Natl. Acad. Sci. USA* 85:7448–51 (1988)), and the like.

Specific embodiments for the isolation of RRN3 nucleic acids, presented as example but not by way of limitation, are as follows.

For expression cloning (a technique commonly known in the art), an expression library is constructed by methods known in the art. For example, mRNA (e.g., human) is isolated, cDNA is prepared and then ligated into an expression vector (e.g., a bacteriophage derivative) such that it is capable of being expressed by the host cell into which it is then introduced. Various screening assays can then be used to select for the expressed Rrn3 polypeptide. In one embodiment, anti-Rrn3 specific antibodies can be used for selection.

In another embodiment, polymerase chain reaction (PCR) can be used to amplify the desired sequence in a genomic or cDNA library, prior to selection. Oligonucleotide primers representing known RRN3 sequences, for example, as selected from SEQ ID NO:1, can be used as primers in PCR. In a typical embodiment, the oligonucleotide primers represent at least part of the RRN3 conserved segments of strong identity between RRN3 of different species. The synthetic oligonucleotides can be utilized as primers to amplify particular oligonucleotides within the RRN3 gene by PCR sequences from a source (RNA or DNA), typically a cDNA library, of potential interest. PCR can be carried out, for example, by use of a Perkin-Elmer Cetus thermal cycler and Taq polymerase (Gene Amp). The DNA being amplified can include mRNA or cDNA or genomic DNA from any eukaryotic species. One of skill in the art can choose to synthesize several different degenerate primers for use in the PCR reactions. For example, the CODEHOP strategy of Rose et al. (*Nucl. Acids Res.* 26:1628–35 (1998), which is incorporated by reference herein) can be used to design degenerate PCR primers using multiply-aligned sequences as a reference.

It is also possible to vary the stringency of hybridization conditions used in priming the PCR reactions, to allow for greater or lesser degrees of nucleotide sequence similarity between the known RRN3 nucleotide sequence and the related nucleic acid being isolated. For cross species hybridization, low stringency conditions are typically used. For same species hybridization, moderately stringent conditions are more typically used. After successful amplification of a segment of a related RRN3 nucleic acid, that segment can be molecularly cloned and sequenced, and utilized as a probe to isolate a complete cDNA or genomic clone. This, in turn, can permit the determination of the gene's complete nucleotide sequence, the analysis of its expression, and the production of its polypeptide product for functional analysis, as described infra. In this fashion, additional genes encoding Rrn3 polypeptides and Rrn3 polypeptide derivatives can be identified.

The above-methods are not meant to limit the following general description of methods by which clones of RRN3 nucleic acids or fragments can be obtained. Any eukaryotic cell potentially can serve as the nucleic acid source for the molecular cloning of the RRN3 gene. The nucleic acid sequences encoding RRN3 can be isolated from vertebrate sources including, mammalian sources such as, porcine, bovine, feline, avian, equine, canine and human, as well as additional primate, avian, reptilian, amphibian, and piscine sources, and the like, from non-vertebrate sources, such as insects, worms, nematodes, plants, and the like. The DNA can be obtained by standard procedures known in the art from cloned DNA (e.g., a DNA "library"), by chemical synthesis, by cDNA cloning, or by the cloning of genomic DNA, or fragments thereof, purified from the desired cell. (See, e.g., Sambrook et al., supra; Glover, (ed.), *DNA Cloning: A Practical Approach*, IRL Press, Washington, D.C. Vol. I, II. (1985).) Clones derived from genomic DNA can contain regulatory and intron DNA regions in addition to coding regions; clones derived from cDNA will typically contain only exon sequences. Whatever the source, the nucleic acids can be molecularly cloned into a suitable vector for propagation of those nucleic acids.

In the molecular cloning of the gene from genomic DNA, DNA fragments are generated, some of which will encode a RRN3 gene. The DNA can be cleaved at specific sites using various restriction enzymes. Alternatively, one can use DNase in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific nucleic acid containing the desired gene can be accomplished in a number of ways. For example, a portion of a RRN3 (of any species) gene or its specific RNA, or a fragment thereof can be purified and labeled. The generated DNA fragments can be screened by nucleic acid hybridization to the labeled probe (see, e.g., Benton and Davis, *Science* 196:180–02 (1977); Grunstein and Hogness, *Proc. Natl. Acad. Sci. USA* 72:3961–65 (1975)). Those DNA fragments with substantial identity to the probe will hybridize. It is also possible to identify the appropriate fragment by restriction enzyme digestion(s) and comparison of fragment sizes with those expected according to a known restriction map, if such is available. Further selection can be carried out on the basis of the properties of the gene.

Alternatively, the presence of the RRN3 nucleic acids can be detected by assays based on the physical, chemical, or immunological properties of its expressed product. For example, cDNA clones, or DNA clones which hybrid-select the proper mRNAs, can be selected which produce a polypeptide that, for example, has similar or identical electrophoretic migration, isoelectric focusing behavior, proteolytic digestion maps, promotion of cell proliferation activity, substrate binding activity, or antigenic properties as known for Rrn3 polypeptide(s). Immune serum or antibody which specifically binds to the Rrn3 polypeptide can be used to identify putatively Rrn3 polypeptide synthesizing clones by binding in an immunoassay, (e.g. an ELISA (enzyme-linked immunosorbent assay)-type procedure).

The RRN3 gene can also be identified by mRNA selection by nucleic acid hybridization followed by in vitro translation. In this procedure, fragments are used to isolate complementary mRNAs by hybridization. Such DNA fragments typically represent available, purified RRN3 DNA of another species (e.g., human, mouse, and the like). Immunoprecipitation analyses or functional assays (e.g., stimulation of pol I transcription in vitro) of the in vitro translation products of the isolated mRNAs identifies the mRNA and, therefore, the complementary DNA fragments that contain the desired sequences. In addition, specific mRNAs can be selected by adsorption of polysomes isolated from cells to immobilized antibodies specifically directed against Rrn3 polypeptide. A radiolabeled RRN3 cDNA can be synthesized using the selected mRNA (from the adsorbed polysomes) as a template. The radiolabeled mRNA or cDNA can then be used as a probe to identify the RRN3 DNA from among other genomic DNA.

Alternatives to isolating the RRN3 genomic DNA include, but are not limited to, chemically synthesizing the gene sequence itself from a known sequence or making cDNA to the mRNA which encodes the Rrn3 polypeptide. For example, RNA for cDNA cloning of the RRN3 gene can be isolated from cells that express the Rrn3 polypeptide. Other methods are possible and are considered within the scope of the invention.

The identified and isolated RRN3 nucleic acids can then be inserted into an appropriate cloning vector. A large number of vector-host systems known in the art can be used. Possible vectors include, but are not limited to, plasmids or modified viruses. The vector system is selected to be compatible with the host cell. Such vectors include, but are not limited to, bacteriophages such as lambda derivatives, yeast integrative and centromeric vectors, 2µ plasmid, and derivatives thereof, or plasmids such as pBR322, pUC, pcDNA3.1 or pRSET (Invitrogen) plasmid derivatives or the Bluescript vector (Stratagene), to name but a few. The insertion of the RRN3 nucleic acids into a cloning vector can, for example, be accomplished by ligating the DNA fragment into a cloning vector which has complementary cohesive termini. If the complementary restriction sites used to fragment the DNA are not present in the cloning vector, however, the ends of the DNA molecules can be enzymatically modified. Alternatively, any desired restriction endonuclease site can be produced by ligating nucleotide sequences (e.g., linkers) onto the DNA termini; these ligated sequences can comprise specific chemically synthesized oligonucleotides encoding restriction endonuclease recognition sequences. In an alternative method, the cleaved vector and RRN3 nucleic acids can be modified by homopolymeric tailing. Recombinant molecules can be introduced into host cells via transformation, transfection, infection, electroporation, and the like, so that many copies of the nucleic acid sequence are generated.

In an alternative method, the RRN3 nucleic acids can be identified and isolated after insertion into a suitable cloning vector in a "shot gun" approach. Enrichment for the RRN3 nucleic acids, for example, by size fractionation, can be done before insertion into the cloning vector. In specific embodiments, transformation of host cells with recombinant DNA molecules that incorporate the isolated RRN3 gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

Expression of the RRN3 Gene

The nucleotide sequence coding for a Rrn3 polypeptide, or a functionally active derivative, analog or fragment thereof, can be inserted into an appropriate expression vector (i.e., a vector which contains the necessary elements for the transcription and translation of the inserted polypeptide-coding sequence). The necessary transcriptional and translational signals can also be supplied by the native RRN3 gene and/or its flanking regions. A variety of host-vector systems can be utilized to express the polypeptide-coding sequence. These include, but are not limited to, mammalian cell systems infected with virus (e.g., vaccinia virus, adenovirus, and the like), insect cell systems infected with virus (e.g., baculovirus), microorganisms such as yeast containing yeast vectors, or bacteria transformed with bacteriophage DNA, plasmid DNA, or cosmid DNA. The expression elements of vectors vary in their strengths and specificities. Depending on the host-vector system utilized, any one of a number of suitable transcription and translation elements can be used. In specific embodiments, the human RRN3 gene is expressed, or a nucleic acid sequence encoding a functionally active portion of human Rrn3 is expressed in yeast or bacteria. In yet another embodiment, a fragment of RRN3 comprising a domain of the Rrn3 polypeptide is expressed.

Any of the methods previously described for the insertion of DNA fragments into a vector can be used to construct expression vectors containing a chimeric gene consisting of appropriate transcriptional/translational control signals and the polypeptide coding sequences. These methods include in vitro recombinant DNA and synthetic techniques and in vivo recombinants (genetic recombination). Expression of nucleic acid sequences encoding a Rrn3 polypeptide or fragment can be regulated by a second nucleic acid sequence so that the Rrn3 polypeptide or fragment is expressed in a host transformed with the recombinant DNA molecule. For example, expression of a Rrn3 polypeptide can be controlled by any promoter/enhancer element known in the art. Promoters which can be used to control RRN3 gene expression include, but are not limited to, the SV40 early promoter region (Benoist and Chaxnbon, *Nature* 290:304–10 (1981)), the promoter contained in the 3' long terminal repeat of Rous sarcoma virus (Yamamoto et al., *Cell* 22:787–97 (1980)), the herpes thymidine kinase promoter (Wagner et al., *Proc. Nat. Acad. Sci. USA* 78:1441–45 (1981)), the regulatory sequences of the metallothionein gene (Brinster et al., *Nature* 296:39–42 (1982)), prokaryotic expression vectors such as the β-lactamase promoter (Villa-Komaroff et al., *Proc. Natl. Acad. Sci. USA* 75:3727–31 (1978)) or the tac promoter (deBoer et al., *Proc. Natl. Acad. Sci. USA* 80:21–25 (1983)), plant expression vectors including the cauliflower mosaic virus 35S RNA promoter (Gardner et al., *Nucl. Acids Res.* 9:2871–88 (1981)), and the promoter of the photosynthetic enzyme ribulose biphosphate carboxylase (Herrera-Estrella et al., *Nature* 310:115–20 (1984)), promoter elements from yeast or other fungi such as the Gal7 and Gal4 promoters, the ADH (alcohol dehydrogenase) promoter, the PGK (phosphoglycerol kinase) promoter, the alkaline phosphatase promoter, and the like.

The following animal transcriptional control regions, which exhibit tissue specificity, have been utilized for transgenic expression animals: the elastase I gene control region which is active in pancreatic acinar cells (Swift et al., *Cell* 38:639–46 (1984); Ornitz et al., *Cold Spring Harbor Symp. Quant. Biol.* 50:399–409 (1986); MacDonald, *Hepatology* 7(1 Suppl.):42S–51S (1987); the insulin gene control region which is active in pancreatic beta cells (Hanahan, *Nature* 315:115–22 (1985)), the immunoglobulin gene control region which is active in lymphoid cells (Grosschedl et al., *Cell* 38:647–58 (1984); Adams et al., *Nature* 318:533–8 (1985); Alexander et al., *Mol. Cell. Biol.* 7:1436–44 (1987)), the mouse mammary tumor virus control region which is active in testicular, breast, lymphoid and mast cells (Leder et al., *Cell* 45:485–95 (1986)), the albumin gene control region which is active in liver (Pinkert et al., *Genes Dev.* 1:268–76 (1987)), the alpha-fetoprotein gene control region which is active in liver (Krumlauf et al., *Mol. Cell. Biol.* 5:1639–48 (1985); Hammer et al., *Science* 235:53–58 (1987)); the alpha 1-antitrypsin gene control region which is active in the liver (Kelsey et al., *Genes and Devel.* 1:161–71 (1987)); the beta-globin gene control region which is active in myeloid cells (Magram et al., *Nature* 315:338–40 (1985); Kollias et al., *Cell* 46:89–94 (1986)); the myelin basic protein gene control region which is active in oligodendrocyte cells in the brain (Readhead et al., *Cell* 48:703–12 (1987)); the myosin light chain-2 gene control region which is active in skeletal muscle (Shani, *Nature* 314:283–86 (1985)); and the gonadotropic releasing hormone gene control region which is active in the hypothalamus (Mason et al., *Science* 234:1372–78 (1986)).

In a specific embodiment, a vector is used that comprises a promoter operably linked to a RRN3-encoding nucleic acid, one or more origins of replication, and, optionally, one or more selectable markers (e.g., an antibiotic resistance gene). For example, an expression construct can be made by subdloning a RRN3 coding sequence into a restriction site of the pRSECT expression vector. Such a construct allows for the expression of the Rrn3 polypeptide under the control of the T7 promoter with a histidine amino terminal flag sequence for affinity purification of the expressed polypeptide.

Expression vectors containing RRN3 nucleic acid inserts can be identified by general approaches well known to the skilled artisan, including: (a) nucleic acid hybridization, (b) the presence or absence of "marker" gene function, and (c) expression of inserted sequences. In the first approach, the presence of a RRN3 nucleic acid inserted in an expression vector can be detected by nucleic acid hybridization using probes comprising sequences that are homologous to an inserted RRN3 nucleic acid. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, and the like) caused by the insertion of a vector containing the RRN3 nucleic acids. For example, if the RRN3 nucleic acid is inserted within the marker gene sequence of the vector, recombinants containing the RRN3 insert can be identified by the absence of marker gene function.

In the third approach, recombinant expression vectors can be identified by assaying the Rrn3 polypeptide expressed by the recombinant. Such assays can be based, for example, on the physical or functional properties of the Rrn3 polypeptide in in vitro assay systems (e.g., binding with anti-Rrn3 antibody, promotion of rRNA transcription, and the like). Once a particular recombinant DNA molecule is identified and isolated, several methods that are known in the art can be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain can be chosen that modulates the expression of the inserted sequences, or modifies or processes the gene product in the specific fashion desired. Expression from certain promoters can be elevated in the presence of certain inducers; thus, expression of the genetically engineered Rrn3 polypeptide can be controlled. Furthermore, different host cells having characteristic and specific mechanisms for the translational and post-translational processing and modification (e.g., glycosylation, phosphorylation) of polypeptides can be used. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a mammalian protein. Furthermore, different vector/host expression systems can affect processing reactions to different extents.

Rrn3 Polypeptides, Fragments, Derivatives and Analogs

The invention further relates to Rrn3 polypeptides, fragments, derivatives and analogs thereof. In one aspect, the invention provides amino acid sequences of Rrn3 polypeptide, typically human Rrn3 polypeptide (SEQ ID NO:2). In particular aspects, the polypeptides, fragments, derivatives, or analogs of Rrn3 polypeptides are from an animal (e.g., human, mouse, rat, pig, cow, dog, monkey, and the like). The production and use of Rrn3 polypeptides, fragments, derivatives and analogs thereof are also within the scope of the present invention. In a specific embodiment, the fragment, derivative or analog is functionally active (i.e., capable of exhibiting one or more functional activities associated with a full-length, wild-type Rrn3 polypeptide). As one example, such fragments, derivatives or analogs which have the desired immunogenicity or antigenicity can be used, for example, in immunoassays, for immunization, for inhibition of Rrn3 activity, and the like. Fragments, derivatives or analogs that retain, or alternatively lack or inhibit, a desired Rrn3 property of interest (e.g., binding to a Rrn3 binding partner, stimulation of rRNA transcription, or modulation (e.g., inhibition or stimulation) of cell proliferation) can be used as inducers, or inhibitors of such property and its physiological correlates. A specific embodiment relates to a Rrn3 fragment that can be bound by an anti-Rrn3 antibody. Fragments, derivatives or analogs of Rrn3 can be tested for the desired activity by procedures known in the art, including but not limited to the functional assays described herein.

Rrn3 polypeptide derivatives include naturally-occurring amino acid sequence variants as well as those altered by substitution, addition or deletion of one or more amino acid residues that provide for functionally active molecules. Rrn3 polypeptide derivatives include, but are not limited to, those containing as a primary amino acid sequence of all or part of the amino acid sequence of a Rrn3 polypeptide including altered sequences in which one or more functionally equivalent amino acid residues (e.g., a conservative substitution) are substituted for residues within the sequence, resulting in a silent change.

In another aspect, Rrn3 polypeptides include those peptides having one or more consensus amino acid sequences shared by all Rrn3 family members, but not found in other proteins. These regions are conserved in both sequence and length and display the general consensus:

(1) Tyr(Ile/Leu)(Ala/Gly)(Ala/Ser)(Phe/Tyr)(Ile/Leu)(Ala/Ser)ArgAlaLys;

(2) PheTyr(Ala/Ser)XaaXaaGln(Ala/Ser)(Ile/Leu)XaaXaaXaa (Phe)XaaPheArg; and (3) PhePro(Phe/Tyr)AspXaaXaaXaaLeu(Lys);

where parentheses indicate positions which vary among family members, and Xaa indicates variable positions. Database analysis indicates that these consensus sequences are not found in other polypeptides, and therefore this evolutionary conservation reflects the pol I-specific function of Rrn3 polypeptides. Rrn3 family members, including Rrn3 polypeptides, fragments, derivatives and/or analogs comprising one or more of these consensus sequences, are also within the scope of the invention. In a preferred embodiment, the Rrn3 family member is other than *Saccharomyces cerevisiae* Rrn3 polypeptide.

In another aspect, a polypeptide consisting of or comprising a fragment of a Rrn3 polypeptide having at least 10 contiguous amino acids of the Rrn3 polypeptide is provided. In other embodiments, the fragment consists of at least 20 or 50 contiguous amino acids of the Rrn3 polypeptide. In a specific embodiment, the fragments are not larger than 35, 100 or even 200 amino acids.

Fragments, derivatives or analogs of Rrn3 polypeptide include but are not limited to those molecules comprising regions that are substantially similar to Rrn3 polypeptide or fragments thereof (e.g., in various embodiments, at least 50%, 60%, 70%, 75%, 80%, 90%, or even 95% identity or similarity over an amino acid sequence of identical size), or when compared to an aligned sequence in which the alignment is done by a computer sequence comparison/alignment program known in the art, or whose coding nucleic acid is capable of hybridizing to a RRN3 nucleic acid, under high stringency, moderate stringency, or low stringency conditions (supra). Rrn3 polypeptides further comprise fragments and derivatives having an antigenic determinant (e.g., can be recognized by an antibody specific for human Rrn3 polypeptide).

The Rrn3 polypeptide derivatives and analogs can be produced by various methods known in the art. The manipulations which result in their production can occur at the gene or protein level. For example, the cloned RRN3 nucleic acids can be modified by any of numerous strategies known in the art (see, e.g., Sambrook et al., supra), such as making conservative substitutions, deletions, insertions, and the like. The sequence can be cleaved at appropriate sites with restriction endonuclease(s), followed by further enzymatic modification if desired, isolated, and ligated in vitro. In the production of the RRN3 nucleic acids encoding a fragment, derivative or analog of a Rrn3 polypeptide, the modified nucleic acid typically remains in the proper translational reading frame, so that the reading frame is not interrupted by translational stop signals or other signals which interfere with the synthesis of the Rrn3 fragment, derivative or analog. The RRN3 nucleic acid can also be mutated in vitro or in vivo to create and/or destroy translation, initiation and/or termination sequences. The Rrn3 encoding nucleic acid can also be mutated to create variations in coding regions and/or to form new restriction endonuclease sites or destroy preexisting ones and to facilitate further in vitro modification. Any technique for mutagenesis known in the art can be used, including but not limited to, chemical mutagenesis, in vitro site-directed mutagenesis (Hutchison et al., *J. Biol. Chem.* 253:6551–60 (1978)), the use of TAB® linkers (Pharmacia), and the like.

Manipulations of the Rrn3 polypeptide sequence can also be made at the polypeptide level. Included within the scope of the invention are Rrn3 polypeptide fragments, derivatives or analogs which are differentially modified during or after synthesis (e.g., in vivo or in vitro translation). Such modifications include conservative substitution, glycosylation, acetylation, phosphorylation, amidation, derivatization by known protecting/blocking groups, proteolytic cleavage, linkage to an antibody molecule or other cellular ligand, and the like. Any of numerous chemical modifications can be carried out by known techniques, including, but not limited to, specific chemical cleavage (e.g., by cyanogen bromide), enzymatic cleavage (e.g., by trypsin, chymotrypsin, papain, V8 protease, and the like); modification by, for example, $NaBH_4$ acetylation, formylation, oxidation and reduction, or metabolic synthesis in the presence of tunicamycin, and the like.

In addition, fragments, derivatives and analogs of Rrn3 polypeptides can be chemically synthesized. For example, a peptide corresponding to a portion, or fragment, of a Rrn3 polypeptide, which comprises a desired domain, or which mediates a desired activity in vitro, can be synthesized by use of chemical synthetic methods using, for example, an automated peptide synthesizer. Furthermore, if desired, non-classical amino acids or chemical amino acid analogs can be introduced as a substitution or addition into the Rrn3 polypeptide sequence. Non-classical amino acids include but are not limited to the D-isomers of the common amino acids, α-amino isobutyric acid, 4-aminobutyric acid, 2-amino butyric acid, γ-amino butyric acid, ε-Ahx, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

In a specific embodiment, the Rrn3 fragment or derivative is a chimeric, or fusion, protein comprising a Rrn3 polypeptide or fragment thereof (typically consisting of at least a domain or motif of the Rrn3 polypeptide, or at least 10 contiguous amino acids of the Rrn3 polypeptide) joined at its amino- or carboxy-terminus via a peptide bond to an amino acid sequence of a different protein. In one embodiment, such a chimeric protein is produced by recombinant expression of a nucleic acid encoding the protein. The chimeric product can be made by ligating the appropriate nucleic acid sequence, encoding the desired amino acid sequences, to each other in the proper coding frame and expressing the chimeric product by methods commonly known in the art. Alternatively, the chimeric product can be made by protein synthetic techniques (e.g., by use of an automated peptide synthesizer).

Rrn3 polypeptides can be isolated and purified by standard methods including chromatography (e.g., ion exchange, affinity, sizing column chromatography, high pressure liquid chromatography), centrifugation, differential solubility, or by any other standard technique for the purification of proteins. The functional properties can be evaluated using any suitable assay as described herein or otherwise known to the skilled artisan. Alternatively, once a Rrn3 polypeptide produced by a recombinant is identified, the amino acid sequence of the polypeptide can be deduced from the nucleotide sequence of the chimeric gene contained in the recombinant. As a result, the protein can be synthesized by standard chemical methods known in the art (see, e.g., Hunkapiller et al., *Nature* 310:105–11 (1984); Stewart and Young, *Solid Phase Peptide Synthesis*, $2^{nd}$ Ed., Pierce Chemical Co., Rockford, Ill., (1984)).

In another alternate embodiment, native Rrn3 polypeptides can be purified from natural sources by standard methods such as those described above (e.g., immunoaffinity purification). In a specific embodiment of the present invention, Rrn3 polypeptides, whether produced by recombinant DNA techniques, by chemical synthetic methods or by purification of native polypeptides, include but are not limited to those containing as a primary amino acid sequence all or part of the amino acid sequence of human Rrn3 polypeptide (SEQ ID NO:2), as well as fragments, derivatives and analogs thereof.

Structure of the RRN3 Gene and Polypeptide(s)

The structure of the RRN3 gene and Rrn3 polypeptide can be analyzed by various methods known in the art. The cloned DNA or cDNA corresponding to the RRN3 gene can be analyzed by methods including but not limited to Southern hybridization (Southern, *J. Mol. Biol.* 98:503–17 (1975)), Northern hybridization (see, e.g., Freeman et al., *Proc. Natl. Acad. Sci. USA* 80:4094–98 (1983)), restriction endonuclease mapping (see generally Sambrook et al., supra), and DNA sequence analysis (see, e.g., Sambrook et al., supra). Polymerase chain reaction (PCR; see, e.g., U.S. Pat. Nos. 4,683,202, 4,683,195 and 4,889,818; Gyllensten et al., *Proc. Natl. Acad. Sci. USA* 85:7652–56 (1988); Ochman et al., *Genetics* 120:621–3 (1988); Loh et al., *Science*

243:217–20 (1989)) followed by Southern hybridization with a RRN3-specific probe can allow the detection of the RRN3 gene in DNA from various cell types. Methods of amplification other than PCR are commonly known and can also be employed.

In one embodiment, Southern blot hybridization can be used to determine the genetic linkage of the RRN3 locus. Northern blot hybridization analysis can be used to determine the expression of the RRN3 gene. Various cell types at various states of development or activity can be tested for RRN3 expression. The stringency of the hybridization conditions for both Southern and Northern blot hybridization can be manipulated to ensure detection of nucleic acids with the desired degree of sequence identity to the specific RRN3 probe used. Modifications of these and other methods commonly known in the art can be used. Restriction endonuclease mapping can be used to roughly determine the genetic structure of the RRN3 gene. Restriction maps derived by restriction endonuclease cleavage can be confirmed by DNA sequence analysis. DNA sequence analysis can be performed by any techniques known in the art, including but not limited to the method of Maxam and Gilbert (*Meth. Enzymol.* 65:499–560 (1980)), the Sanger dideoxy method (Sanger et al., *Proc. Natl. Acad. Sci. USA* 74:5463–67 (1977)), the use of T7 DNA polymerase (Tabor and Richardson, U.S. Pat. No. 4,795,699), or use of an automated DNA sequencer (e.g., Applied Biosystems, Foster City, Calif.).

The amino acid sequence of the Rrn3 polypeptide can be derived by deduction from the DNA sequence, or alternatively, by direct sequencing of the protein (e.g., with an automated amino acid sequencer). The Rrn3 polypeptide sequence can be further characterized by a hydrophilicity analysis (Hopp and Woods, *Proc. Natl. Acad. Sci. USA* 78:3824–28 (1981)). A hydrophilicity profile can be used to identify the hydrophobic and hydrophilic regions of the Rrn3 polypeptide and the corresponding regions of the gene sequence which encode such regions.

Secondary structural analysis (e.g., Chou and Fasman, *Biochemistry* 13:222–45 (1974)) can also be conducted to identify regions of the Rrn3 polypeptide that assume specific secondary structures. Manipulation, translation, and secondary structure prediction, open reading frame prediction and plotting, as well as determination of sequence identity and similarities, can also be accomplished using computer software programs available in the art, such as those described above. Other methods of structural analysis can also be employed. These include but are not limited to X-ray crystallography (Engstom, *Biochem. Exp. Biol.* 11:7–13 (1974)) and computer modeling (Fletterick and Zoller, (eds.), "Computer Graphics and Molecular Modeling", In *Current Communications in Molecular Biology*, Cold Spring Harbor Laboratory, Cold Spring Harbor, N.Y. (1986); Bordo, *Comput. Appl. Biosci.* 9:639–45 (1993); Bruccoleri and Karpus, *Biopolymers* 26:137–68 (1987); Hansen et al. *Pac. Symp. Biocomput.* 106–17 (1998)); Li et al., *Protein Sci.* 6:956–70 (1997); Sternberg and Zvelebil, *Eur. J. Cancer* 26:1163–66 (1990); Ring and Cohen, *FASEB J.* 7:783–90 (1993); and Sutcliffe et al., *Protein Eng.* 1:377–84 (1987)).

Antibodies to Rrn3 Polypeptides, Fragments. Derivatives and Analogs

Rrn3 polypeptides, fragments, derivatives, and analogs thereof, can be used as an immunogen to generate antibodies which immunospecifically bind such Rrn3 polypeptides, fragments, derivatives, and analogs thereof. Such antibodies include but are not limited to polyclonal antibodies, monoclonal antibodies, chimeric antibodies, single chain antibodies, heavy chain antibody fragments (e.g., F(ab'), F(ab')$_2$, Fv, or hypervariable regions), and an Fab expression library. In a specific embodiment, polyclonal and/or monoclonal antibodies to whole, intact human Rrn3 polypeptide are produced. In another embodiment, antibodies to a domain of a human Rrn3 polypeptide are produced. In another embodiment, fragments of a human Rrn3 polypeptide identified as hydrophilic are used as immunogens for antibody production.

Methods for making and using antibodies are generally disclosed by Harlow and Lane (Using Antibodies, A Laboratory Manual, Cold Spring Harbor Laboratory, Cold Spring Harbor, N.Y. (1999); the disclosure of which is incorporated by reference herein). Various procedures known in the art can be used for the production of polyclonal antibodies to a Rrn3 polypeptide, fragment, derivative or analog thereof. For the production of such antibodies, various host animals (including, but not limited to, rabbits, mice, rats, sheep, goats, camals, llamas and the like) can be immunized by injection with the native Rrn3 polypeptide, fragment, derivative or analog. Various adjuvants can be used to increase the immunological response, depending on the host species, including but not limited to Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monoclonal antibodies directed toward a Rrn3 polypeptide, fragment, derivative, or analog thereof, any technique which provides for the production of antibody molecules by continuous cell lines in culture can also be used. Such techniques include, for example, the hybridoma technique originally developed by Kohler and Milstein (see, e.g., *Nature* 256:495–97 (1975)), as well as the trioma technique, (see, e.g., Hagiwara and Yuasa, Hum. Antibodies Hybridomas 4:15–19 (1993)), the human B-cell hybridoma technique (see, e.g., Kozbor et al., *Immunology Today* 4:72 (1983)), and the EBV-hybridoma technique to produce human monoclonal antibodies (see, e.g., Cole et al., In *Monoclonal Antibodies and Cancer Therapy*, Alan R. Liss, Inc., pp. 77–96 (1985)). Human antibodies can be used and can be obtained by using human hybridomas (see, e.g., Cote et al., *Proc. Natl. Acad. Sci. USA* 80:2026–30 (1983)) or by transforming human B cells with EBV virus in vitro (see, e.g., Cole et al., supra).

Further to the invention, "chimeric" or "humanized" antibodies (see, e.g., Morrison et al., *Proc. Natl. Acad. Sci. USA* 81:6851–5 (1984); Neuberger et al., *Nature* 312:604–08 (1984); Takeda et al., *Nature* 314:452–4 (1985)) can be prepared. Such chimeric antibodies are typically prepared by splicing the non-human genes for an antibody molecule specific for a Rrn3 polypeptide together with genes from a human antibody molecule of appropriate biological activity. It can be desirable to transfer the antigen binding regions (e.g., F(ab')$_2$, F(ab'), Fv, or hypervariable regions) of non-human antibodies into the framework of a human antibody by recombinant DNA techniques to produce a substantially human molecule. Methods for producing such "chimeric" molecules are generally well known and described in, for example, U.S. Pat. Nos. 4,816,567; 4,816,397; 5,693,762; and 5,712,120; International Patent Publications WO 87/02671 and WO 90/00616; and European Patent Publication EP 239 400; the disclosures of which are incorporated by reference herein). Alternatively, a human monoclonal antibody or portions thereof can be identified by first screening a human B-cell cDNA library for DNA molecules that encode antibodies that specifically bind to an Rrn3 polypeptide according to the method generally set forth by Huse et al. (*Science* 246:1275–81 (1989)). The DNA molecule can then be cloned and amplified to obtain sequences that encode the antibody (or binding domain) of the desired specificity. Phage display technology offers another technique for selecting antibodies that bind to Rrn3 polypeptides, fragments, derivatives or analogs thereof. (See, e.g., International Patent Publications WO 91/17271 and WO 92/01047; and Huse et al., supra).

According to another aspect of the invention, techniques described for the production of single chain antibodies (see, e.g., U.S. Pat. Nos. 4,946,778 and 5,969,108) can be adapted to produce Rrn3-specific single chain antibodies. An additional aspect of the invention utilizes the techniques described for the construction of a Fab expression library (see, e.g., Huse et al. (1989) supra) to allow rapid and easy identification of monoclonal Fab fragments with the desired specificity for Rrn3 polypeptides, fragments, derivatives, or analogs thereof.

The immunoglobulins also can be heavy chain antibodies. Immunoglobulins from animals such as camels, dromedaries, and llamas (Tylopoda) can form heavy chain antibodies, which comprise heavy chains without light chains. (See, e.g., Desmyter et al., J. Biol. Chem. 276:26285–90 (2001); Muyldermans and Lauwereys, J. Mol. Recognit. 12:131–40 (1999); Arbabi Ghahroudi et al., FEBS Lett. 414:521–26 (1997); Muyldermans et al., Protein Eng. 7:1129–35 (1994); Hamers-Casterman et al., Nature 363:446–48 (1993); the disclosures of which are incorporated by reference herein.) The variable region of heavy chain antibodies are typically referred to as "VHH" regions. (See, e.g., Muyldermans et al., TIBS 26:230–35 (2001).) The VHH of heavy chain antibodies typically have enlarged or altered CDR regions, as such enlarged CDR1 and/or CDR3 regions. Methods of producing heavy chain antibodies are also known in the art. (See, e.g., Arbabi Ghahroudi et al., supra; Muyldermans and Lauwereys, supra.)

Antibody which contains the idiotype of the molecule can be generated by known techniques. For example, such fragments include but are not limited to, the F(ab')$_2$ fragment which can be produced by pepsin digestion of the antibody molecule, the Fab' fragments which can be generated by reducing the disulfide bridges of the F(ab')$_2$ fragment, the Fab fragments which can be generated by treating the antibody molecule with papain and a reducing agent, and Fv fragments. Recombinant Fv fragments can also be produced in eukaryotic cells using, for example, the methods described in U.S. Pat. No. 5,965,405.

In the production of antibodies, screening for the desired antibody can be accomplished by techniques known in the art (e.g., ELISA (enzyme-linked immunosorbent assay)). In one example, antibodies which recognize a specific domain of a Rrn3 polypeptide can be used to assay generated hybridomas for a product which binds to a Rrn3 fragment containing that domain. For selection of an antibody that specifically binds to a first Rrn3 polypeptide derivative, but which does not specifically bind a different Rrn3 polypeptide, one can select on the basis of antibody positive binding to the first Rrn3 polypeptide and a lack of antibody binding to the second different Rrn3 polypeptide.

Antibodies specific to a domain of Rrn3 polypeptides are also provided. The foregoing antibodies can be used in methods known in the art relating to the localization and activity of the Rrn3 polypeptide sequences of the invention (e.g., for imaging proteins, measuring levels thereof in appropriate physiological samples, in diagnostic methods, and the like). In another embodiment of the invention (see infra), anti-Rrn3 antibodies and fragments thereof containing the antigen-binding domain are used as agents and compositions to slow or abate the growth of proliferative disease.

Functional Assays for Rrn3 Polypeptides, Fragments, Derivatives, and Analogs

The functional activity of Rrn3 polypeptides, fragments, derivatives and analogs can be assayed by various methods. For example, when assaying for the ability to bind or compete with wild-type Rrn3 polypeptide for binding to anti-Rrn3 antibody, various immunoassays known in the art can be used. Such assays include, but are not limited to, competitive and non-competitive assay systems using techniques such as radioimmunoassays, ELISA (enzyme linked immunosorbent assay) "sandwich" immunoassays, immunoradiometric assays, gel diffusion precipitin reactions, immunodiffusion assays, in situ immunoassays (using colloidal gold, enzyme or radioisotope labels, and the like), Western blots, precipitation reactions, agglutination assays (e.g., gel agglutination assays, hemagglutination assays), complement fixation assays, immunofluorescence assays, protein A assays, immunoelectrophoresis assays, and the like. (See generally Harlow and Lane, supra). Antibody binding can be detected by measuring a label on the primary antibody. Alternatively, the primary antibody is detected by measuring binding of a secondary antibody or reagent to the primary antibody. The secondary antibody can also be directly labeled. Many means are known in the art for detecting binding in an immunoassay and are considered within the scope of the present invention.

In another embodiment, the ability of Rrn3 polypeptide to stimulate rRNA transcription is assayed. For example, transcription stimulation can be measured by the method of Klein and Grummt (*Proc. Natl. Acad. Sci. USA* 96:6096–101 (1999). Briefly, standard transcription reactions (25 $\mu$l), containing 25 $\mu$g of a whole cell extract of protein from mammalian cells, include 25 ng of rRNA template (e.g., the human or mouse rRNA sequences)/12 mM Tris-HCl, pH 7.9/0.1 mM EDTA/0.5 mM dithioerythritol/5 mM MgCl$_2$/80 mM KCl/12% glycerol/0.66 each ATP, CTP, and GTP/0.01 mM UTP with 1 $\mu$Ci of [$\alpha$-$^{32}$P]UTP (3,000 Ci/mmol). Transcription is performed for 60 minutes at 30° C. After completion of transcription, the amount of transcription is quantitated by known methods, such as by separating the unincorporated radioactively labeled nucleotides from the labeled transcripts and then counting in a scintillation counter or by separation using gel electrophoresis. In such assays, the endogenous Rrn3 polypeptide can be depleted by anti-Rrn3 antibody.

In still another embodiment, the functional activity of a Rrn3 polypeptide, fragment, derivative, or analog is determined in an in vivo system. For example, stimulation of rRNA transcription or physiological changes in cells or tissues can be measured and correlated with Rrn3 activity by expressing RRN3 nucleic acids in mammalian cells and examining the effect on cell proliferation. Alternatively, Rrn3 polypeptides, fragments, derivatives, or analogs can be expressed in a heterologous system and the activity of the Rrn3 polypeptide, fragment, derivative or analog assayed as a physiological changes in that system. For example, the ability of a Rrn3 polypeptide to stimulate rRNA transcription in vivo can be tested using the yeast plasmid shuffling system. In particular, a yeast strain that has a null allele of the endogenous RRN3 gene can be rescued by an extrachromosomal copy of the yeast RRN3 gene, or a heterologous RRN3 nucleic acid from another eukaryotic organism. For example, the ability of the heterologous (e.g., human) RRN3 nucleic acid to complement the yeast RRN3 null allele can be determined. Similarly, the activity of a Rrn3 fragment, derivative or analog can be determined by the same complementation assay. The activity of mutant RRN3 nucleic acids can also be determined. Other eukaryotic RRN3 genes can also be isolated by complementation of the yeast null allele, as will be appreciated by the skilled artisan.

In Vivo Uses of RRN3 Nucleic Acids, Rrn3 Polypeptides, Fragments, Derivatives, Analogs and Antibodies The invention provides further for methods for the administration of one or more agents, or compositions containing such agents, which modulate cell proliferation. Such agents include, but are not limited to, Rrn3 polypeptides, fragments, derivatives and analogs thereof as described hereinabove; antibodies specific for Rrn3 polypeptide, fragments, derivatives and analogs thereof (as described hereinabove); nucleic acids encoding Rrn3 polypeptides, fragments, derivatives and analogs thereof (as described hereinabove); RRN3 antisense nucleic acids, and Rrn3 polypeptide agonists and antagonists. The Rrn3 agents can be used to treat disorders involving cell hyperproliferation (e.g., tumorigenesis) or hypoproliferation by altering Rrn3 function.

Generally, it is typical to administer an agent of a species origin or species reactivity (in the case of antibodies) that is the same as that of the recipient. Thus, a human Rrn3 polypeptide, fragment, derivative, or analog thereof, or RRN3 nucleic acid or fragment or analog thereof, or an antibody to a human Rrn3 polypeptide, is administered to a human in a dose which is therapeutically or prophylactically effective.

Diseases involving cell hyperproliferation are treated or prevented, for example, by administration of an agent that decreases Rrn3 function. Examples of such an agent include, but are not limited to, anti-sense RRN3 nucleic acids under the control of a strong inducible promoter, particularly those that are active in inhibiting cell proliferation. Other agents that can be used to decrease Rrn3 activity include anti-Rrn3 antibodies, or those that can be identified using in vitro assays or animal models, examples of which are described herein.

In specific embodiments, agents that decrease RRN3 function are administered therapeutically (including prophylactically) in diseases involving an increased (relative to normal or desired) level of Rrn3 polypeptide or function. For example, the agent can be administered to a patient where Rrn3 polypeptide is overexpressed, genetically defective, or biologically hyperactive, as compared with a normal cell of that type. Further, an agent of the invention can be administered in diseases or disorders wherein in vitro (or in vivo) assays indicate the utility of Rrn3 antagonist administration. For example, RRN3 gene function can be specifically targeted to cancer cells to kill those cells.

The level in Rrn3 polypeptide or function can be detected, for example, by obtaining a patient tissue sample (such as from a biopsy tissue) and assaying it in vitro for RNA or polypeptide levels, structure and/or activity of the expressed RRN3 RNA or Rrn3 polypeptide. Many methods standard in the art can be thus employed including, but not limited to, immunoassays to detect and/or visualize Rrn3 polypeptide (e.g., Western blot, immunoprecipitation followed by sodium dodecyl sulfate polyacrylamide gel electrophoresis ("SDS PAGE"), immunocytochemistry, and the like) and/or hybridization assays to detect RRN3 expression by detecting and/or visualizing RRN3 mRNA (e.g., Northern blot assays, dot blots, in situ hybridization, quantitative reverse transcriptase-PCR, and the like), among others known to the skilled artisan.

Diseases involving cell hyperproliferation that can be treated or prevented include but are not limited to malignancies, premalignant conditions (e.g., hyperplasia, metaplasia, dysplasia), benign tumors, hyperproliferative disorders, benign dysproliferative disorders, and the like. In specific embodiment, an agent of the invention is administered to a human patient to prevent progression to cancer. Diseases involving cell hypoproliferation that can be treated or prevented include but are not limited to cardiac disease and other conditions in which an increase in cell proliferation is desired.

Gene Therapy

RRN3 nucleic acids of the present invention can be used in the process of gene therapy. Gene therapy refers to the process of providing for the expression of nucleic acid sequences of exogenous origin in a subject for the treatment of a disease within that subject. In a specific embodiment, anti-sense nucleic acids complementary to a sequence encoding a Rrn3 polypeptide, fragment, derivative or analog thereof, are administered to inhibit RRN3 gene function, by way of gene therapy. In another embodiment, nucleic acids encoding Rrn3 polypeptide, or a fragment, derivative or analog thereof, are administered to repair a defective RRN3 gene, or to stimulate RRN3 gene activity. Any of the methods for gene therapy available in the art can be used according to the present invention. Exemplary methods are described below.

For general reviews of the methods of gene therapy, see Goldspiel et al. (*Clin. Pharm.* 12:488–505 (1993)); Wu and Wu (*Biotherapy* 3:87–95 (1991)); Tolstoshev (*Ann. Rev. Pharmacol. Toxicol.* 32:573–96 (1993)); Mulligan (*Science* 260:926–32 (1993)); Morgan and Anderson (*Ann. Rev. Biochem.* 62:191–217 (1993)); and May (*TIBTECH* 11:155–215 (1993)).

Methods commonly known in the art of recombinant DNA technology that can be used include those described in Ausubel et al. (supra) and Kriegler (*Gene Transfer and Expression, A Laboratory Manual*, Stockton Press, NY (1990)). In one embodiment, the agent comprises a RRN3 sense nucleic acid that is part of an expression vector that expresses a Rrn3 polypeptide or fragment or chimeric protein thereof in a suitable host cell. In particular, such a nucleic acid has a promoter operably linked to the RRN3 coding region, the promoter being inducible or constitutive, and, optionally, tissue-specific. In another embodiment, the agent comprises a RRN3 antisense nucleic acid that is part of an expression vector that expresses the antisense nucleic acid in a suitable host. In particular, such an antisense nucleic acid has a promoter operably linked to the RRN3 antisense nucleic acid, the promoter being inducible or constitutive, and, optionally, tissue-specific.

In another particular embodiment, a nucleic acid is used in which the RRN3 coding sequences and any other desired sequences are flanked by regions that promote homologous recombination at a desired site in the genome, thus providing for intrachromosomal expression of the RRN3 nucleic acid (see, e.g., Koller and Smithies, *Proc. Natl. Acad. Sci. USA* 86:8932–35 (1989); Zijlstra et al., *Nature* 342:435–38 (1989); U.S. Pat. Nos. 5,631,153; 5,627,059; 5,487,992; and 5,464,764)). RRN3 nucleic acids that are dysfunctional (e.g., due to a heterologous (non-RRN3 sequence) insertion within the RRN3 coding sequence) can be used to "knockout" endogenous RRN3 function by homologous recombination (see, e.g., Capecchi, *Science* 244:1288–92 (1989); U.S. Pat.

Nos. 5,631,153; 5,627,059; 5,487,992; and 5,464,764)). In a specific embodiment of the invention, a nucleic acid containing a portion of a RRN3 gene, in which the RRN3 sequences flank, both 5' and 3', a different gene sequence, is used to disrupt the expression of an RRN3 gene by homologous recombination (see Koller and Smithies, (supra); Zijlstra et al. (supra).

For any of these embodiments, delivery of the nucleic acid into a patient can be either direct, in which case the patient is directly exposed to the nucleic acid or nucleic acid-carrying vector, or indirect, in which case cells are first transformed with the nucleic acid in vitro, then transplanted into the patient. These two approaches are known, respectively, as in vivo or ex vivo gene therapy. In a specific embodiment, the nucleic acid is directly administered in vivo, where it is expressed to produce the encoded product. This can be accomplished by any of numerous methods known in the art (e.g., by constructing it as part of an appropriate nucleic acid expression vector and administering it so that it becomes intracellular, for example, by infection using a defective or attenuated retroviral or other viral vector (see, e.g., U.S. Pat. No. 4,980,286), by direct injection of naked DNA, or by use of microparticle bombardment, such as a gene gun (BIOLISTIC™, Dupont). DNA can also be inserted into cells by coating naked DNA with lipids or cell-surface receptors or transfecting agents, encapsulation in liposomes, microparticles, or microcapsules, or by administering the DNA in linkage to a peptide which is known to enter the nucleus, by administering the DNA in linkage to a ligand subject to receptor-mediated endocytosis (see, e.g., Wu and Wu, *J. Biol. Chem.* 262:4429–32 (1987)), which can be used to target cell types specifically expressing the receptors, and the like. In another embodiment, a nucleic acid-ligand complex can be formed in which the ligand comprises a fusogenic viral peptide to disrupt endosomes, allowing the nucleic acid to avoid lysosomal degradation.

In yet another embodiment, the nucleic acid can be targeted in vivo for cell specific uptake and expression, by targeting a specific receptor (see, e.g., International Patent Publications WO 92/06180; WO 92/22635; WO 92/20316; WO 93/14188; and WO 93/20221). Alternatively, the nucleic acid can be introduced intracellularly and incorporated within host cell DNA for expression by homologous recombination (see, e.g., Koller and Smithies supra; Zijlstra et al. supra; U.S. Pat. Nos. 5,631,153; 5,627,059; 5,487,992; and 5,464,764).

In a specific embodiment, a viral vector is used that contains the RRN3 nucleic acid (sense or antisense). For example, a retroviral vector can be used (see Miller et al., *Meth. Enzymol.* 217:581–99 (1993)). These retroviral vectors are typically modified to delete retroviral sequences that are not necessary for packaging of the viral genome and integration into host cell DNA. The RRN3 nucleic acid to be used in gene therapy is cloned into the vector, which facilitates delivery of the nucleic acid into a patient. More detail about retroviral vectors can be found in Boesen et al. (*Biotherapy* 6:291–302 (1994)), which describes the use of a retroviral vector to deliver the mdrl gene to hematopoietic stem cells in order to make the stem cells more resistant to chemotherapy. Lentiviral vectors can also be used. (See, e.g., Naldini et al., *Science* 272:263–67 (1996).) Other references illustrating the use of viral vectors in gene therapy are: Clowes et al. (*J. Clin. Invest.* 93:644–51 (1994)); Kiem et al. (*Blood* 83:1467–73 (1994)); Salmons and Gunzberg (*Hum Gene Ther.* 4:129–41 (1993)); and Grossman and Wilson (*Curr. Opin. Genet Dev.* 3:110–14 (1993)).

Adenoviruses can also be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are prostate, liver, the central nervous system, endothelial cells, and muscle. Adenoviruses have the advantage of being capable of infecting non-dividing cells. Kozarsky and Wilson (*Curr. Opin. Genet Dev.* 3:499–503 (1993)) present a review of adenovirus-based gene therapy. Bout et al. (*Human Gene Therapy* 5:3–10 (1994)) demonstrated the use of adenovirus vectors to transfer genes to the respiratory epithelia of rhesus monkeys. Herman et al. (*Human Gene Therapy* 10:1239–49 (1999)) describe the intraprostatic injection of a replication-deficient adenovirus containing the herpes simplex thymidine kinase gene into human prostate, followed by intravenous administration of the prodrug ganciclovir in a phase I clinical trial. Other instances of the use of adenoviruses in gene therapy can be found in Rosenfeld et al. (*Science* 252:431–34 (1991)); Rosenfeld et al. (*Cell* 68:143–55 (1992)); Mastrangeli et al. (*J. Clin. Invest.* 91:225–34 (1993)); and Thompson (*Oncol. Res* 11:1–8 (1999)). Adeno-associated virus (AAV) can also be used in gene therapy (see, e.g., Ali et al., *Gene Therapy* 1:367–84 (1994); U.S. Pat. Nos. 4,797,368 and 5,139,941; Walsh et al., *Proc. Soc. Exp. Biol. Med.* 204:289–300 (1993); Grimm et al., *Human Gene Therapy* 10:2445–50 (1999)).

Another approach to gene therapy involves transferring a gene to cells in tissue culture by methods such as electroporation, lipofection, calcium phosphate mediated transfection, or viral infection. Typically, the method of transfer includes the transfer of a selectable marker to the cells. The cells are then placed under selection to isolate those cells that have taken up and are expressing the transferred gene. The selected cells are then delivered to a patient.

In one embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid, cell fusion, chromosome-mediated gene transfer, microcell-mediated gene transfer, and the like. Numerous techniques are known in the art for the introduction of foreign genes into cells (see, e.g., Loeffler and Behr, *Meth. Enzymol.* 217:599–618 (1993); Cotten et al., *Meth. Enzymol.* 217:618–44 (1993); Cline, *Pharmacol. Ther.* 29:69–92 (1985)) and can be used in accordance with the present invention. The technique typically provides for the stable transfer of the nucleic acid to the cell, so that the nucleic acid is expressible by the cell and is heritable and expressible by its cell progeny.

The resulting recombinant cells can be delivered to a patient by various methods known in the art. Typically, cells are injected subcutaneously. In another embodiment, recombinant skin cells can be applied as a skin graft onto the patient. Recombinant blood cells (e.g., hematopoietic stem or progenitor cells) are typically administered intravenously. The amount of cells required for use depends on the desired effect, the patient's condition, and the like, and can be determined by one skilled in the art.

Cells into which a RRN3 nucleic acid can be introduced for purposes of gene therapy encompass any desired, available cell type, and include but are not limited to breast cells, prostate cells, epithelial cells, endothelial cells, keratinocytes, fibroblasts, muscle cells, hepatocytes, blood cells (such as T lymphocytes, B lymphocytes, monocytes, macrophages, neutrophils, eosinophils, megakaryocytes, granulocytes), and various stem or progenitor cells (in particular, hematopoietic stem or progenitor cells, such as those obtained from bone marrow, umbilical cord blood, peripheral blood, fetal liver, and the like). The cells used for gene therapy generally are autologous to the patient, but heterologous cells that can be typed for compatibility with the patient can be used.

Antisense Regulation of RRN3 Expression

In other embodiments, Rrn3 function is inhibited by use of RRN3 antisense nucleic acids. The present invention provides for the administration of nucleic acids of at least six nucleotides that are antisense to a gene or cDNA encoding Rrn3, or a portion thereof, to inhibit the function of Rrn3 polypeptide. A RRN3 "antisense" nucleic acid as used herein refers to a nucleic acid which hybridizes to a portion of a RRN3 RNA (typically mRNA) by virtue of some sequence complementarity. The antisense nucleic acid can be complementary to a coding and/or noncoding region of a RRN3 mRNA. Such antisense nucleic acids have utility as agents that inhibit Rrn3 function, and can be used in the treatment or prevention of disorders, as described supra.

The antisense nucleic acids can be oligonucleotides that are double-stranded or single-stranded, RNA or DNA, or a derivative or analog thereof, which can be directly administered to a cell, or which can be produced intracellularly by transcription of exogenous, introduced nucleic acid sequences.

In a specific embodiment, the RRN3 antisense nucleic acid provided by the instant invention can be used to prevent tumor or other forms of aberrant cell proliferation. The invention further provides pharmaceutical compositions comprising an effective amount of the RRN3 antisense nucleic acids of the invention in a pharmaceutically acceptable carrier, as described infra. In another embodiment, the invention is directed to methods for inhibiting the expression of a RRN3 nucleic acid sequence in a eukaryotic cell comprising providing the cell with an effective amount of a composition comprising a RRN3 antisense nucleic acid. RRN3 antisense nucleic acids and their uses are described in detail below.

RRN3 Antisense Nucleic Acids

The RRN3 antisense nucleic acids are of at least six nucleotides and are typically oligonucleotides (ranging from 6 to about 50 nucleotides or more). In specific aspects, the oligonucleotide is at least 10 nucleotides, at least 15 nucleotides, at least 100 nucleotides, or can be at least 200 nucleotides. The oligonucleotides can be DNA or RNA or chimeric mixtures or derivatives or analogs thereof, and can be single-stranded or double-stranded. The oligonucleotide can be modified at the base moiety, sugar moiety, and/or phosphate backbone. The oligonucleotide can include other appending groups such as peptides, or agents facilitating transport across the cell membrane (see, e.g., Letsinger et al., *Proc. Natl. Acad. Sci. USA* 86:6553–56 (1989); Lemaitre et al., *Proc. Natl. Acad. Sci. USA* 84:648–52 (1987); International Patent Publication WO 88/09810) or blood-brain barrier (see, e.g., International Patent Publication WO 89/10134), hybridization-triggered cleavage agents (see, e.g., Krol et al., *BioTechniques* 6:958–76 (1988)) or intercalating agents (see, e.g., Zon, *Pharm. Res.* 5:539–49 (1988)).

In one embodiment of the invention, a RRN3 antisense oligonucleotide is provided, typically as single-stranded DNA. The oligonucleotide can be modified at any position on its structure with substituents generally known in the art.

The RRN3 antisense oligonucleotide can comprise at least one modified base moiety, such as, for example, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylamino-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, 2,6-diaminopurine, and the like. In another embodiment, the oligonucleotide comprises at least one modified sugar moiety, such as, for example, arabinose, 2-fluoroarabinose, xylulose, or hexose.

In yet another embodiment, the oligonucleotide comprises at least one modified phosphate backbone, such as, for example, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (see Gautier et al., *Nucl. Acids Res.* 15:6625–41 (1987)). The oligonucleotide can be conjugated to another molecule (e.g., a peptide, hybridization triggered cross-linking agent, transport agent, hybridization-triggered cleavage agent, and the like).

Antisense oligonucleotides of the invention can be synthesized by standard methods known in the art (e.g., by use of a commercially available automated DNA synthesizer). As examples, phosphorothioate oligonucleotides can be synthesized by the method of Stein et al. (*Nucl. Acids Res.* 16:3209–21 (1988)), methyphosphonate oligonucleotides can be prepared by use of controlled pore glass polymer supports (Sarin et al., *Proc. Natl. Acad. Sci. USA* 85:7448–51 (1988)), and the like.

In a specific embodiment, the RRN3 antisense oligonucleotide comprises catalytic RNA, or a ribozyme (see, e.g., International Patent Publication WO 90/11364; Sarver et al., *Science* 247:1222–25 (1990)). In another embodiment, the oligonucleotide is a 2'-0-methylribonucleotide (Inoue et al., *Nucl. Acids Res.* 15:6131–48 (1987)), or a chimeric RNA-DNA analogue (Inoue et al., *FEBS Lett.* 215:327–30 (1987)).

In another specific embodiment, double-stranded RNA directs the sequence-specific degradation of mRNA by RNA interference. (See generally Hunter, *Curr. Biol.* 10:R137–40 (2000); Bosher and Labouesse, *Nat. Cell. Biol.* 2:e31–36 (2000).) Briefly, double-stranded RRN3 nucleic acids are introduced into a cell to selectively inhibit RRN3 gene expression by causing degradation of the RRN3 mRNA. (See, e.g., Zamore et al., *Cell* 101:25–33 (2000).)

In an alternative embodiment, the RRN3 antisense nucleic acid of the invention is produced intracellularly by gene therapy (supra). For example, a vector can be introduced in vivo such that it is taken up by a cell, within which cell the vector or a portion thereof is transcribed, producing an antisense nucleic acid (RNA) of the invention. The vector would contain a sequence encoding the RRN3 antisense nucleic acid or a portion thereof. Once inside the cell the vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art and used for replication and expression in mammalian cells. Expression of the nucleic acid encoding the RRN3 antisense RNA can be controlled by any promoter known in the art to act in mammalian, typically human, cells. The promoters can be inducible or constitutive. Inducible promoters include but are not limited to, the SV40 early promoter region (Benoist and Chambon supra), the promoter contained in the 3' long terminal repeat of Rous sarcoma virus (Yamamoto et al. supra), the herpes thymidine kinase promoter (Wagner et al. supra), the regulatory sequences of the metallothionein gene (Brinster et al. supra), and the like.

Use of RRN3 Antisense Nucleic Acids

The antisense nucleic acids of the invention comprise a sequence complementary to at least a portion of an RNA transcript of a RRN3 gene, such as a human RRN3 gene. Absolute complementarity, although typical, is not required, however. A sequence "complementary to at least a portion of an RNA," as used herein, means a sequence having sufficient complementarity to be able to hybridize with the RNA, forming a stable duplex. In the case of double-stranded RRN3 antisense nucleic acids, a single strand of the duplex DNA can be tested, or triplex formation can be assayed. The ability to hybridize will depend on both the degree of complementarity and the length of the antisense nucleic acid. Generally, the longer the hybridizing nucleic acid, the more base mismatches it can contain and still form a stable duplex (or triplex, as the case may be). One skilled in the art can ascertain a tolerable degree of mismatch by use of standard procedures to determine the melting point of the hybridized complex.

The RRN3 antisense nucleic acids can be administered to an individual to treat (or prevent) diseases of a cell type that expresses or overexpresses Rrn3 polypeptide or as a method to selectively inactivate certain cells by inhibiting production of Rrn3 polypeptide. In a specific embodiment, such a disease is hyperproliferation, such as cancer or tumor formation. In one embodiment, a single-stranded DNA antisense RRN3 oligonucleotide is used. Cell types which express or overexpress RRN3 RNA can be identified by various methods known in the art. Additionally, cell types which exhibit hyperproliferation due to other defects can also be identified by various methods known in the art. Such methods include, but are not limited to, hybridization with a RRN3-specific nucleic acid (e.g., by Northern blot hybridization, dot blot hybridization or in situ hybridization), observing the ability of RNA from the cell to be translated in vitro into Rrn3 polypeptide, immunoassay, and the like. In a typical example, primary tissue from a patient can be assayed for RRN3 expression prior to treatment, for example, by immunocytochemistry or in situ hybridization. Similarly, methods for detecting hyperproliferation due to over- or under-expression of other genes can also be identified by various methods known in the art. RRN3 antisense nucleic acids can be used to treat any of these diseases.

Compositions of the invention, including an effective amount of a RRN3 antisense nucleic acid in a pharmaceutically acceptable carrier, can be administered to a patient having a disease which is of a type that expresses or overexpresses RRN3 RNA or Rrn3 polypeptide. The amount of RRN3 antisense nucleic acid which will be effective in the treatment of a particular disease will depend on the nature of the disease, and can be determined by standard clinical techniques. Where possible, it is typical to determine the antisense cytotoxicity of the cell type to be treated in vitro, and then in useful animal model systems prior to testing and use in humans.

In a specific embodiment, compositions comprising RRN3 antisense nucleic acids and a pharmaceutically acceptable carrier are administered via liposomes, microparticles, or microcapsules, as well as any other delivery modes described herein. In various embodiments of the invention, it can be useful to use such compositions to achieve sustained release of the RRN3 antisense nucleic acids. In a specific embodiment liposomes targeted via antibodies to specific identifiable tumor antigens are utilized (see, e.g., Leonetti et al., Proc. Natl. Acad. Sci. USA 87:2448–51 (1990); Renneisen et al., J. Biol. Chem. 265:16337–42 (1990)).

Treatment and Prevention of Hyperproliferative and Dysproliferative Disorders

Diseases involving an increase in cell proliferation (growth) or in which cell proliferation is otherwise undesirable, are also treated or prevented by administration of an agent that antagonizes (inhibits) Rrn3 function. In particular, because Rrn3 polypeptide is required for rRNA transcription, agents that interfere with RRN3 gene expression or Rrn3 polypeptide levels or function can be used to treat such diseases. In addition to the agents described above, other agents that can be used further include, but are not limited to, anti-Rrn3 antibodies (and fragments and derivatives thereof containing the antigen binding region thereof). Agents that inhibit Rrn3 function can be identified by use of known convenient in vitro assays (e.g., based on their ability to inhibit binding of Rrn3 polypeptide to another protein or to inhibit any known Rrn3 function, as typically assayed in vitro or in cell culture) can also be employed. Typically, suitable in vitro or in vivo assays are utilized to determine the effect of a specific agent and whether its administration is indicated for treatment of the affected tissue.

Treatment and Prevention of Hypoproliferative Diseases

Diseases involving decreased cell proliferation or in which cell proliferation is desired for treatment or prevention, and that can be treated or prevented by stimulating Rrn3 activity, include but are not limited to degenerative disorders, growth deficiencies, hypoproliferative disorders, physical trauma, lesions, and wounds (for example, to promote wound healing, or to promote regeneration in degenerated, lesioned or injured tissues), and the like. Such diseases can be treated by any of the methods described herein that increase Rrn3 activity or cell proliferation Administration of Agents and Compositions The invention provides methods for the administration to a subject of an effective amount of an agent of the invention. Typically, the agent is substantially purified prior to formulation. The subject can be an animal, including but not limited to, cows, pigs, horses, chickens, cats, dogs, and the like, and is typically a mammal, and in a particular embodiment human. In another specific embodiment, a non-human mammal is the subject.

Formulations and methods of administration that can be employed when the agent comprises a nucleic acid are described above; additional appropriate formulations and routes of administration can be selected from among those described hereinbelow.

Various delivery systems are known and can be used to administer an agent, such as, for example, encapsulation in liposomes, microparticles, microcapsules, recombinant cells capable of expressing the agent, receptor-mediated endocytosis (see, e.g., Wu and Wu, *J. Biol. Chem.* 262:4429–32 (1987)), construction of an agent comprising a nucleic acid as part of a retroviral or other vector, and the like. Methods of introduction include but are not limited to intradermal, intramuscular, intraperitoneal, intravenous, subcutaneous, intranasal, epidural and oral routes. The agents can be administered by any convenient route such as, for example, by infusion or bolus injection, by absorption through epithelial or mucocutaneous linings (e.g., oral mucosa, rectal and intestinal mucosa), and the like, and can be administered together with other functionally active agents. Administration can be systemic or local. In addition, it can be desirable to introduce an agent into the target tissue by any suitable route, including intravenous and intrathecal injection. Pulmonary administration can also be employed, such as, for example, by use of an inhaler or nebulizer, and formulation of the agent with an aerosolizing agent.

In a specific embodiment, it can be desirable to administer the agent locally to the area in need of treatment; this administration can be achieved by, for example, and not by way of limitation, local infusion during surgery, topical application (e.g., in conjunction with a wound dressing after surgery), by injection, by means of a catheter, by means of a suppository, or by means of an implant, the implant being of a porous, non-porous, or gelatinous material, including membranes such as sialastic membranes, or fibers. In one embodiment, administration can be by direct injection at the site (or former site) of a malignant tumor or neoplastic or pre-neoplastic tissue.

In another embodiment, the agent can be delivered in a vesicle, in particular a liposome (see, e.g., Langer, *Science* 249:1527–33 (1990); Treat et al., In, *Liposomes in the Therapy of Infectious Disease and Cancer*, Lopez-Berestein and Fidler (eds.), Liss, N.Y., pp. 353–65 (1989); Lopez-Berestein, supra, pp. 317–27).

In yet another embodiment, the agent can be delivered in a controlled release system. In one embodiment, a pump can be used (see, e.g., Langer, supra; Sefton, *Crit. Ref. Biomed. Eng.* 14:201–40 (1987); Buchwald et al., *Surgery* 88:507–16 (1980); Saudek et al., *N. Engl. J. Med.* 321:574–79 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, N.Y. (1984); Ranger and Peppas, *J. Macromol. Sci. Rev. Macromol. Chem.* 23:61-(1983); see also Levy et al., *Science* 228:190–92 (1985); During et al., *Ann. Neurol.* 25:351–56 (1989); Howard et al., *J. Neurosurg.* 71:105–12 (1989)). In yet another embodiment, a controlled release system can be placed in proximity of the therapeutic target, thus requiring only a fraction of the systemic dose (see, e.g., Goodson, in *Medical Applications of Controlled Release*, supra, Vol. 2, pp. 115–38 (1984)). Other controlled release systems are discussed in, for example, the review by Langer (*Science* 249:1527–33 (1990)).

Where the agent is a nucleic acid encoding a Rrn3 polypeptide, the nucleic acid can be administered in vivo to promote expression of its encoded polypeptide, by constructing it as part of an appropriate nucleic acid expression vector and administering it so that it becomes intracellular, for example, by use of a retroviral vector (see U.S. Pat. No. 4,980,286), or by direct injection, or by use of microparticle bombardment (e.g., a gene gun; BIOLISTIC™, Dupont), or coating with lipids or cell-surface receptors or transfecting agents, or by administering it in linkage to a homeobox-like peptide which is known to enter the nucleus (see, e.g., Joliot et al., *Proc. Natl. Acad. Sci. USA* 88:1864–68 (1991)), and the like. Other modes of in vivo and ex vivo administration are described supra. Alternatively, an agent which comprises a nucleic acid can be introduced intracellularly and incorporated within host cell DNA for expression by homologous recombination as described above.

The present invention also provides pharmaceutical compositions. Such compositions comprise a therapeutically effective amount of an agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more typically in humans. The term "carrier" refers to a diluent, adjuvant, excipient, stabilizer, or vehicle with which the agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Pharmaceutical compositions can take the form of solutions, suspensions, emulsion, tablets, pills, capsules, powders, sustained-release formulations, and the like. The composition can be formulated as a suppository, with traditional binders and carriers such as triglycerides.

Oral formulations can include standard carriers such as pharmaceutical grades of mannitol, lactose, starch, magnesium stearate, sodium saccharine, cellulose, magnesium carbonate, and the like. Examples of suitable pharmaceutical carriers are described in, for example, *Remington's Pharmaceutical Sciences* (Gennaro (ed.), Mack Publishing Co., Easton, Pa. (1990)). Such compositions will contain a therapeutically effective amount of the agent, typically in purified form, together with a suitable amount of carrier so as to provide a formulation proper for administration to the patient. The formulation should suit the mode of administration.

In one embodiment, the agent is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form. For example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The agents of the invention can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The amount of the agent which will be effective in the treatment of a particular disease as indicated by modulation of cell proliferation will depend on the nature of the disease, and can be determined by standard clinical techniques. In addition, in vitro assays can optionally be employed to help identify optimal dosage ranges. The precise dose of the agent to be employed in the formulation will also depend on the route of administration, and the seriousness of the disease, and should be decided according to the judgment of the practitioner and each patient's circumstances. Suitable dosage ranges for intravenous administration are generally about 20–500 micrograms of active agent per kilogram body weight. Suitable dosage ranges for intranasal administration are generally about 0.01 pg/kg body weight to 1 mg/kg body weight. Effective doses can be extrapolated from dose response curves derived from in vitro or animal model test systems. Suppositories generally contain active ingredient in the range of 0.5% to 10% by weight; oral formulations typically contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Screening

Rrn3 polypeptides and RRN3 nucleic acids, and fragments, derivatives, and analogs thereof, and anti-Rrn3 antibodies, also have utility in diagnostics. Such molecules can be used in assays, such as immunoassays, to detect, prognose, diagnose, or monitor various diseases (including conditions and disorders) affecting RRN3 expression, or to monitor the treatment thereof. In particular, methods, such as an immunoassay, can be carried out by steps comprising contacting a sample derived from a patient with an anti-Rrn3 antibody under conditions conducive to immunospecific binding, and detecting or measuring the amount of any immunospecific binding by the antibody. In a particular aspect, binding of antibody to Rrn3 polypeptide, in tissue sections, can be used to detect aberrant Rrn3 localization or aberrant (e.g., low, absent or elevated) levels of Rrn3 polypeptide. In a specific embodiment, antibody to Rrn3 polypeptide can be used to assay a patient tissue or serum sample for the presence of Rrn3, where an aberrant level of Rrn3 is an indication of a disease. By "aberrant levels" is meant increased or decreased levels relative to that present, or a standard level representing that present, in an analogous sample from a portion of the body or from a subject not having the disease.

The immunoassays which can be used include, but are not limited to, competitive and non-competitive assay systems using techniques such as Western blot, radioimmunoassay, ELISA (enzyme linked immunosorbent assay), "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, protein A immunoassay, and the like.

RRN3 genes and related nucleic acid sequences and subsequences, including complementary sequences, can also be used in hybridization assays. RRN3 nucleic acid sequences (e.g., SEQ ID NO:1), or fragments thereof comprising about at least 8 nucleotides, can be used as hybridization probes. Hybridization assays can be used to detect, prognose, diagnose, or monitor disease (including conditions and disorders) associated with aberrant changes in RRN3 expression and/or activity, as described supra. In particular, a hybridization assay is carried out by a method comprising contacting a sample containing polynucleotides with a nucleic acid probe capable of hybridizing to RRN3 DNA or RNA, under conditions such that hybridization can occur, and detecting or measuring any resulting hybridization.

In specific embodiments, diseases involving hypo- or hyper-proliferation of cells can be diagnosed, or their suspected presence can be screened for, or a predisposition to develop such diseases can be identified by detecting decreased or increased levels of Rrn3 polypeptide, RRN3 RNA, or Rrn3 functional activity. Additionally, hypo- or hyper-proliferation can be diagnosed by detecting mutations in RRN3 RNA or DNA or Rrn3 polypeptide (e.g., translocations in RRN3 nucleic acids, truncations in the RRN3 gene or Rrn3 polypeptide, changes in nucleotide or amino acid sequence relative to wild-type RRN3, or Rrn3, respectively) that cause decreased or increased expression or activity of Rrn3 polypeptide.

By way of example, levels of Rrn3 polypeptide in a biopsy can be detected by immunoassay; levels of RRN3 RNA can be detected by hybridization assays (e.g., Northern blot or dot blot). Translocations and point mutations in RRN3 nucleic acids can be detected by Southern blot, RFLP analysis, SSCP analysis, PCR using primers that typically generate a fragment spanning at least most of the RRN3 gene, sequencing of the RRN3 genomic DNA or cDNA obtained from the sample, and the like.

In one embodiment, levels of RRN3 mRNA or Rrn3 polypeptide in a sample of a tissue isolated from a patient are detected or measured, in which increased levels indicate that the subject has, or has a predisposition to developing, a malignancy or hyperproliferative disease of that tissue, and in which the increased levels are relative to the levels present in an analogous sample from a portion of the body or from a subject not having the malignancy or other hyperproliferative disease, as the case may be.

In another specific embodiment, diseases involving a deficiency in cell proliferation or in which cell proliferation is desirable for treatment, are diagnosed, or their suspected presence can be screened for, or a predisposition to develop such diseases can be detected, by detecting decreased levels of Rrn3 polypeptide or RRN3 mRNA. Additionally, a deficiency in cell proliferation can be diagnosed by detecting Rrn3 functional activity, or by detecting mutations in RRN3 RNA or DNA or Rrn3 polypeptide (for example, translocations in RRN3 nucleic acids, truncations in the gene or polypeptide, changes in nucleotide or amino acid sequence relative to wild-type RRN3 gene or Rrn3 polypeptide) that cause decreased expression or activity of Rrn3. By way of example, levels of Rrn3 polypeptide, levels of RRN3 mRNA, Rrn3 binding activity, and the presence of translocations or point mutations in the RRN3 gene can be determined as described above.

In a specific embodiment, levels of RRN3 mRNA or Rrn3 polypeptide in a patient sample are detected or measured, in which decreased levels indicate that the subject has, or has a predisposition to developing, a hypoproliferative disorder, in which the decreased levels are relative to the levels present in an analogous sample from a portion of the body or from a subject not having the hypoproliferative disorder, as the case may be.

Kits for diagnostic use are also provided that include, in one or more containers, an anti-Rrn3 antibody and, optionally, a labeled binding partner to the antibody. Alternatively, the anti-Rrn3 antibody can be labeled with a detectable marker (e.g., a chemiluminescent, enzymatic, fluorescent, radioactive moiety, and the like). A kit is also provided that includes, in one or more containers, a nucleic acid probe capable of hybridizing to RRN3 mRNA.

In a specific embodiment, a kit can include, in one or more containers a pair of primers (e.g., each in the size range of 6–30 nucleotides or more) that are capable of priming amplification (e.g., by polymerase chain reaction (see, e.g., Innis et al., PCR Protocols, Academic Press, Inc., San Diego, Calif. (1989)), ligase chain reaction (see, e.g., EP 320 308), use of Qβ replicase, cyclic 5' probe reaction, or other methods known in the art) under appropriate reaction conditions such that at least a portion of a RRN3 nucleic acid is amplified. A kit can optionally further comprise in a container a predetermined amount of a purified Rrn3 polypeptide or RRN3 nucleic acid, for example, for use as a standard or control.

Screening for Agonists and Antagonists

RRN3 nucleic acids, Rrn3 polypeptide, and fragments, derivatives and analogs thereof, also have uses in screening assays to detect candidate compounds that specifically bind to RRN3 nucleic acids, Rrn3 polypeptides, or fragments, derivatives or analogs thereof, and thus have use as agonists or antagonists. The agonists and antagonists can be identified by in vitro and/or in vivo assays. Such assays can be used to identify agents that are therapeutically effective, such as anti-proliferative agents, or as lead compounds for drug development. The invention thus provides assays to detect candidate compounds that specifically affect the activity or expression of RRN3 nucleic acids, Rrn3 polypeptides, or fragments, derivatives or analogs thereof.

In a typical in vivo assay, recombinant cells expressing RRN3 nucleic acids can be used to screen candidate compounds for those that affect RRN3 expression. Effects on RRN3 expression can include transcription of mRNA, translation of the mRNA, synthesis of Rrn3 polypeptides, effects on Rrn3 polypeptide function (e.g., rRNA synthesis) and on Rrn3 polypeptide stability or localization. Such effects on RRN3 expression can be identified as physiological changes, such as, for example, changes in cell growth rate, division or viability. In one embodiment, candidate compounds are administered to recombinant cells expressing Rrn3 polypeptide to identify those compounds that produce a physiological change. In another embodiment, the method comprises administering a candidate compound to a first cell that expresses a first Rrn3 polypeptide; administering the candidate compound to a second cell that expresses a second Rrn3 polypeptide; and determining whether the candidate compound modulates the activity of the first Rrn3 polypeptide but not the activity of the second Rrn3 polypeptide. For example, the first Rrn3 polypeptide can be yeast Rrn3 polypeptide and the second can be human Rrn3 polypeptide. Alternatively, the first Rrn3 polypeptide can be a mutant, and the second Rrn3 polypeptide can be wild-type.

In another embodiment, the yeast plasmid shuffling system allows the identification of agonists and antagonists that specifically affect expression of one Rrn3 polypeptide, but not another Rrn3 polypeptide. In a particular embodiment, a yeast strain that has a null allele of the endogenous yeast RRN3 gene is rescued by an extrachromosomal copy of the yeast RRN3 gene, or a RRN3 nucleic acid from another eukaryotic organism. By screening essentially isogenic yeast strains, which differ only by the RRN3 gene, agonists and antagonists can be identified which are specific for one eukaryotic RRN3 nucleic acid or Rrn3 polypeptide, but not another RRN3 nucleic acid or Rrn3 polypeptide. For example, yeast strains having a null allele of the endogenous yeast RRN3 gene, and having either the human RRN3 cDNA or the Candida albicans RRN3 gene, could be screened for antifungal agents that specifically affect the fungal polypeptide. Similarly, agonists and antagonists can be identified that affect a particular allele or other derivative of a RRN3 nucleic acid or Rrn3 polypeptide. For example, congenic mammalian cells, differing only in the RRN3 gene or Rrn3 polypeptide, can be screened for candidate compounds that affect cell growth, viability and/or cell division.

In another embodiment, the two-hybrid system for selecting interacting proteins in yeast (see, e.g., Fields and Song, Nature 340:245–46 (1989); Chien et al., Proc. Natl. Acad. Sci. USA 88:9578–82 (1991)) can be used to identify candidate compounds that specifically bind to a Rrn3 polypeptide or derivative.

Candidate compounds can also be identified by in vitro screens. For example, recombinant cells expressing RRN3 nucleic acids can be used to recombinantly produce Rrn3 polypeptide for in vitro assays to identify candidate compounds that bind to Rrn3 polypeptide. Candidate compounds (such as putative binding partners of Rrn3 or small molecules) are contacted with the Rrn3 polypeptide (or fragment, derivative or analog thereof) under conditions conducive to binding, and then candidate compounds that specifically bind to the Rrn3 polypeptide are identified. Similar methods can be used to screen for candidate compounds that bind to nucleic acids encoding RRN3, or a fragment, derivative or analog thereof. Methods that can be used to carry out the foregoing are commonly known in the art, and include diversity libraries, such as random or combinatorial peptide or non-peptide libraries that can be screened for candidate compounds that specifically bind to Rrn3 polypeptide. Many libraries are known in the art, such as, for example, chemically synthesized libraries, recombinant phage display libraries, and in vitro translation-based libraries.

Examples of chemically synthesized libraries are described in Fodor et al. (Science 251:767–73 (1991)), Houghten et al. (Nature 354:84–86 (1991)), Lam et al. (Nature 354:82–84 (1991)), Medynski (Bio/Technology 12:709–10 (1994)), Gallop et al. (J. Med. Chem. 37:1233–51 (1994)), Ohlmeyer et al. (Proc. Natl. Acad. Sci. USA 90:10922–26 (1993)), Erb et al., (Proc. Natl. Acad. Sci. USA 91:11422–26 (1994)), Houghten et al. (Biotechniques 13:412–21 (1992)), Jayawickreme et al. (Proc. Natl. Acad. Sci. USA 91:1614–18 (1994)), Salmon et al. (Proc. Natl. Acad. Sci. USA 90:11708–12 (1993)), International Patent Publication WO 93/20242, and Brenner and Lerner (Proc. Natl. Acad. Sci. USA 89:5381–83 (1992)).

Examples of phage display libraries are described in Scott and Smith (Science 249:386–90 (1990)), Devlin et al. (Science 249:404–06 (1990)), Christian et al. (J. Mol. Biol.

227:711–18 (1992)), Lenstra (*J. Immunol. Meth.* 152:149–57 (1992)), Kay et al. (*Gene* 128:59–65 (1993)), and International Patent Publication WO 94/18318.

In vitro translation-based libraries include, but are not limited to, those described in International Patent Publication WO 91/05058, and Mattheakis et al. (*Proc. Natl. Acad. Sci. USA* 91:9022–26 (1994)). By way of examples of nonpeptide libraries, a benzodiazepine library (see, e.g., Bunin et al., *Proc. Natl. Acad. Sci. USA* 91:4708–12 (1994)) can be adapted for use. Peptide libraries (see, e.g., Simon et al., *Proc. Natl. Acad. Sci. USA* 89:9367–71(1992)) can also be used. Another example of a library that can be used, in which the amide functionalities in peptides have been permethylated to generate a chemically transformed combinatorial library, is described by Ostresh et al. (*Proc. Natl. Acad. Sci. USA* 91:11138–42 (1994)).

Screening of the libraries can be accomplished by any of a variety of commonly known methods. See, for example, the following references, which disclose screening of peptide libraries: Parmley and Smith (*Adv. Exp. Med. Biol.* 251:215–18 (1989)); Scott and Smith (supra); Fowlkes et al. (*BioTechniques* 13:422–28 (1992)); Oldenburg et al. (*Proc. Natl. Acad. Sci. USA* 89:5393–97 (1992)); Yu et al. (*Cell* 76:933–45 (1994)); Staudt et al. (*Science* 241:577–80 (1988)); Bock et al. (*Nature* 355:564–66 (1992)); Tuerk et al. (*Proc. Natl. Acad. Sci. USA* 89:6988–92 (1992)); Ellington et al. (*Nature* 355:850–52 (1992)); U.S. Pat. Nos. 5,096,815, 5,223,409, and 5,198,346, all to Ladner et al.; Rebar and Pabo (*Science* 263:671–73 (1994)); and International Patent Publication WO 94/18318.

In a specific embodiment, screening can be carried out by contacting the library members with a Rrn3 polypeptide (or nucleic acid or derivative) immobilized on a solid phase and harvesting those library members that bind to the polypeptide (or nucleic acid or derivative). Examples of such screening methods, termed "panning" techniques are described by way of example in Parmley and Smith (*Gene* 73:305–18 (1988)); Fowlkes et al. (supra); International Patent Publication WO 94/18318; and in references cited hereinabove.

Animal Models

The invention also provides animal models. In one embodiment, animal models for diseases involving cell hypoproliferation are provided. Such an animal can be initially produced by promoting homologous recombination between a RRN3 gene in its chromosome and an exogenous RRN3 nucleic acid that has been rendered biologically inactive (typically by insertion of a heterologous sequence, such as an antibiotic resistance gene). In one aspect, homologous recombination is carried out by transforming embryo-derived stem (ES) cells with a vector containing the insertionally inactivated RRN3 gene, such that homologous recombination occurs, followed by injecting the ES cells into a blastocyst, and implanting the blastocyst into a foster mother, followed by the birth of the chimeric animal ("knockout animal") in which a RRN3 gene has been inactivated (see Capecchi, *Science* 244:1288–92 (1989)). The chimeric animal can be bred to produce additional knockout animals. Such animals can be mice, rats, hamsters, sheep, pigs, cattle, and the like, and are typically non-human mammals. In a specific embodiment, a knockout mouse is produced. Knockout animals are expected to develop, or be predisposed to developing diseases, involving cell hypoproliferation and can be useful to screen for or test candidate compounds for the ability to promote proliferation and thus treat or prevent such diseases.

In a different embodiment of the invention, transgenic animals that have incorporated and express a functional RRN3 gene have use as animal models of diseases involving cell hyperproliferation or malignancy. Transgenic animals are expected to develop or be predisposed to developing diseases involving cell hyperproliferation (e.g., malignancy) and thus can have use as animal models of such diseases (e.g., to screen for or test candidate compounds, such as potential anti-proliferation agents) for the ability to inhibit hyperproliferation (e.g., tumor formation) and thus treat or prevent such diseases.

The following examples are provided merely as illustrative of various aspects of the invention and shall not be construed to limit the invention in any way.

Example 1

Cloning of Human RRN3 cDNA

A BLAST search of the human Expressed Sequence Tag (EST) database using the yeast Rrn3 polypeptide sequence identified informative overlapping EST's (gb|AA481295; gb|AA191111; gb|N42382; gb|H43196; and gb|AA319333; which correspond to nucleotides 1233–854; 1129–1548; 1289–1546; 1621–1431; and 1554–1861 of SEQ ID NO:1) which encode a protein fragment with sequence similarity to amino acids 360 to 532 of the yeast Rrn3 transcription factor. Primers derived from the EST sequences were used to isolate a partial cDNA from human Jurkat cell RNA by reverse transcriptase-polymerase chain reaction ("RT-PCR"). Briefly, an oligonucleotide primer hRACE 5'.2: 5'-TGATTGCAGCAAAAAAGTTAACCACTGA-3'; SEQ ID NO:3) complementary to the polynucleotide sequence encoding amino acids 508–517 of human Rrn3 was used to prime a first strand cDNA synthesis from 1 μg of total cell RNA (a gift of A. M. Hajjar, University of Washington) using Superscript reverse transcriptase (Gibco-BRL). Subsequent PCR with Pfu polymerase (Stratagene) using a gene-internal primer (hRACE 3'.1: 5'-CTATATCGCGACCTGATAAACATCTTTG-3'; SEQ ID NO:4), which corresponds to amino acids 343–352, and the hRACE 5'.2 primer (supra) produced PCR product which was inserted into the PCR vector pCR-BLUNT (Invitrogen) to construct clone h3-2. DNA sequence analysis of this product confirmed that it was identical to the contiguous EST sequence.

The nucleotide sequence of this ORF-internal fragment (encoding amino acids 343 to 517 of the human polypeptide) was used to design primers to isolate further 5' and 3' sequence. The 5' end of the human mRNA was obtained by RT-PCR using a 5'RACE kit (Gibco). An oligonucleotide complementary to the 5' region of clone h3-2 (hRACE5'.3: 5'-CAAAGATGTTTATCAGGTCGCGATATAG; SEQ ID NO:5) was used to prime cDNA synthesis from human Jurkat cell RNA, and the cDNA product was purified, tailed and amplified by PCR according to the manufacturer's instructions. TdT-dependent PCR products derived from a single round of PCR amplification were cloned into the pCR-BLUNT vector to produce construct h5-L.

5'RACE generated two cDNA products which apparently arise from alternatively spliced mRNAs. Both cDNAs share identical 5' sequences including an initiator methionine preceded by an in-frame stop codon, indicating that they encode the N-terminus of the polypeptide and that they are transcribed from the same promoter. The longer product contains an additional 90 base pairs of sequence encoding amino acids 85 to 114 of the human polypeptide. Since this region shares sequence similarity with yeast Rrn3, the longer cDNA was used for further analysis.

The 3' region of the human RRN3 open reading frame was isolated by 3' RACE as follows: a poly A anchor oligonucleotide (Clontech) complementary to the 5' region of the poly A tail was used to prime a reverse transcription reaction using 1 μg of total RNA as described above. The resultant cDNAs were amplified by PCR using the gene-specific primer hRACE3'.1:5' (SEQ ID NO:4) and the Clontech anchor primer. Subsequent analysis of the amplification products revealed that the 3' end of the open reading frame was missing. To determine the 3' end of the open reading frame, the partial human RRN3 cDNA was used as a reference sequence to search the human dbEST databank. The longest EST identified by this search, gb|AA319333 (which corresponds to nucleotides 1554–1861 of SEQ ID NO:1), encodes an additional 70 amino acids which extend the sequence alignment of the human protein to within 8 amino acids of the yeast C-terminus, but does not appear to contain the stop codon identifying the end of the RRN3 coding region.

To facilitate subsequent expression of the RRN3 cDNA, a primer was designed which inserted a translational stop codon adjacent to the final conserved amino acid (glutamate 587). Briefly, the PCR products were secondarily amplified by nested PCR using primers hRACE3'.2: (5'-GGAAGCTTTTTGGCAAGAGCTAAA TTTATTCCTC-3'; SEQ ID NO:6) (encoding amino acids 410–419) and the EST AA319333 primer (5' GCGGATCC<u>TCA</u>TTCAGCACT CATGTCTTCCCATACCTGATA-3': stop codon underlined; SEQ ID NO:7) to produce a ~500 base pair PCR product which was cloned into the pCR-BLUNT vector. Three independent clones of all PCR products described above were sequenced to avoid possible PCR generated errors. The EST AA319333 primer was used in conjunction with the ORF-internal 5' primer hRACE 3'.1 to amplify the sequence encoding the conserved C-terminal region of the human protein.

The resultant cDNA fragments were joined at overlapping restriction enzyme sites to produce a polynucleotide encoding a 587 amino acid polypeptide. Briefly, the human RRN3 open reading frame was constructed by joining the three partial cDNA clones. The h5-L construct was cut at SacI site within the pCR-BLUNT vector, a blunt end created with Klenow enzyme, and the 3' end cleaved at an internal NruI site to generate a fragment which was inserted at the EcoRV and NruI sites of clone h3–2. The PCR product encoding the C-terminal region was then ligated at an internal HindIII site to generate the human RRN3 construct used for further study. The integrity of the human RRN3 ORF was confirmed by DNA sequence analysis.

Example 2

A recently reported human EST (gb|AW239267, which corresponds to nucleotides 1661 to 2068 of SEQ ID NO:1) encodes an additional 3' portion of the human RRN3 cDNA. The full length cDNA thus encodes a polypeptide of 651 amino acids with a predicted molecular mass of 74 kD, which is similar to that of TIF-LA. The sequence of the human RRN3 open reading frame has been deposited in the GenBank database (Accession No. AF227 156).

Example 3

Genetic Locus for RRN3

The RRN3 gene most likely has a single genetic locus. RT-PCR using the 5' and 3' primers adjacent the 5' and 3' ends of the open reading frame generates a product of the expected size and sequence. The cDNA sequence is contained within a genomic fragment of human chromosome region 16p12 spanning approximately 26 kb which is found on two independent bacterial artificial chromosomes ("BAC") clones (gb|AF001549 and gb|AC017077). All of the human EST sequences that were identified were correlated with these BAC clones.

Example 4

Preparation of Anti-Yeast Rrn3 Polypeptide Antibodies

The C-terminal region of yeast RRN3 gene (residues 352–627) was subcloned into the pRSETC expression vector (Invitrogen) to generate a 6His-tagged fusion protein. This construct was transformed into *E. coli* strain UBS520, cultured in TBG/M9 medium containing both ampicillin and kanamycin (0.1 mg/ml) to A600=0.8, and protein expression was induced by addition of IPTG. The ~30 kD recombinant protein was isolated 3 hours post induction using Talon affinity resin (Clontech) under denaturing conditions according to the manufacturer's instructions. The protein was further purified by SDS-PAGE.

The excised gel slices were used for immunization of rabbits (R&R Rabbitry), according to standard methods. Antisera were fractionated by addition of solid ammonium sulfate to 50% saturation, the precipitate collected by centrifugation at 18 k for 20 minutes in an SS-34 rotor, resuspended in 2 pellet volumes of 1×TBS, and dialyzed against 1×TBS overnight at 40° C.

Antiserum was used at a 1/2000 dilution in Western blots performed as described in Lin et al. (*Mol. Cell. Biol.* 16:6436–43 (1996)). For Western blot analysis, the bacterial cells were grown and expression was induced as described above except that 50 ml of medium was cultured, and lysates were prepared by boiling the harvested cells in SDS-PAGE buffer. Proteins were visualized using anti-His monoclonal antibodies (Qiagen) according the manufacturer's instructions.

Example 5

Immune Cross-Reactivity of Human and Yeast Rrn3 Polypeptide

To confirm that the human cDNA encodes a polypeptide which is related to yeast Rrn3, the human and yeast RRN3 cDNAs were expressed in *E. coli* as 6-His fusion proteins and subjected to Western blot analysis. Full length yeast or human RRN3 coding sequences were subcloned into pRSET vector (Invitrogen) to generate 6-His tagged proteins for expression in *E. coli*.

Crude lysates prepared from bacteria expressing either the yeast gene or human cDNA or from cells transformed with the empty expression vector (pREST) were resolved by SDS-PAGE and then transferred to a hybridization membrane. The membrane was probed with anti-His monoclonal antibodies (Qiagen) or with antiserum generated against the C-terminal half of recombinant yeast Rrn3 (described in Example 4). The signal intensities obtained using antibodies against the 6-His tag were used to normalize the amount of recombinant protein loaded. Anti-His antibodies recognized polypeptides of 72 kD and 68 kD in lysates from cells expressing the yeast and human cDNAs, respectively, while no signal is observed in the lysate from the empty vector control. When these lysates were probed with antibodies generated against yeast Rrn3, the human polypeptide was more efficiently detected than the yeast polypeptide. This difference in recognition may be due to limited proteolysis of yeast Rrn3 C-terminus, since it is less stably expressed in bacteria than the human polypeptide. No signal is observed in the empty vector control lysate, however, indicating that the human polypeptide is specifically recognized by the anti-yeast Rrn3 serum, and it is clear from the strength of the observed cross-reaction signal that the yeast and human polypeptides are immunologically conserved.

Example 6

Construction of a Yeast RRN3 Null Allele

To determine whether the human Rrn3 polypeptide could function in yeast, a yeast strain was constructed in which the yeast RRN3 gene was disrupted.

A diploid yeast strain containing a disrupted RRN3 gene was constructed as follows: The coding region of yeast RRN3 was amplified from wild-type yeast genomic DNA and inserted into the pBluT vector (Novagen) to generate RRN3-BluT. RRN3-BluT was digested with EcoRV and PmeI, which cut in the RRN3 coding region, and blunt ends were created using the Klenow fragment. A blunt-ended XhoI/BamHI fragment of the yeast HIS3 gene was inserted into those blunt ends, creating a construct in which base pairs 492 to 1407 of the yeast RRN3 open reading frame were replaced by the yeast HIS3 gene to form an rrn3Δ::HIS3 construct. The HIS3 gene would then act as a marker for the presence of this gene disruption in yeast.

The rrn3Δ::HIS3 construct in RRN3-BluT was digested with SpeI to liberate a linear fragment which was then used to transform diploid wild-type strain W1665a/α (MAT a/α ade2–1 his3–11 leu2–3,112 trp1–1,15 ura3–1 can1–100 RAD5) to His$^+$, creating strain RLY300 (MAT a/α ade2–1 his3–11 leu2–3,112 trp1–1,15 ura3–1 can1–100 RAD5 rrn3Δ::HIS3). Sporulation of this yeast strain and dissection of the resulting spores (tetrads) yielded two viable and two inviable spores. The HIS3 marker was not recovered from viable colonies. This is the expected segregation ratio if the rrn3Δ::HIS3 gene disruption has integrated at the rrn3 locus and has inactivated ("knocked out") the RRN3 gene on one chromosome.

The yeast RRN3 gene was inserted into a yeast expression as follows to create plasmid pRRN3G-425. The coding region of RRN3 was amplified from wild-type yeast genomic DNA and inserted into the pBluT vector (Novagen) to generate RRN3-BluT (described above). 476 base pairs of 5' yeast sequence was PCR-amplified and ligated to the RRN3 open ready frame to produce the construct RRN3G. To express yeast RRN3 from its own promoter, the RRN3G insert was subcloned into the PstI and BamHI sites of pRS425 to create plasmid pRRN3G-425, or into the SpeI and BamHI sites of pRS316 to create plasmid pRRN3G-316. Plasmid pRRN3G-425 carries the LEU2 wildtype gene as a selectable marker and confers the Leu$^+$ phenotype on Leu$^-$ auxotrophic strains.

Yeast strain RLY300 was transformed with pRRN3G-425 to Leu$^+$. Following sporulation of the transformed strain and dissection of the resulting spores, the spores were allowed to germinate on YPD plates. His$^+$ Leu$^+$ colonies were isolated and designated RLY301 (MATa ade2–1 his3–11 leu2–3,112 trp1–1,15 ura3–1 can1–100 RAD5 rrn3Δ::HIS3 [pRRN3G-425]). Proper insertion of the rrn3Δ::HIS3 knockout at the rrn3 locus in the His$^+$ progeny was confirmed by both PCR and Southern blot analysis. When grown under non-selective condition, all His$^+$ colonies retained the LEU2 marker of pRRN3G-425, indicating that the episomal yeast RRN3 gene could substitute for the inactivated yeast RRN3 gene.

To obtain the yeast RRN3 gene on a counterselectable plasmid, the yeast RRN3 gene was subcloned into the URA3 vector RLY302 to create plasmid RRN3G-316. The URA3 gene is counterselectable using 5-fluoroorotic acid. The RRN3G-425 plasmid was exchanged for the RRN3G-316 plasmid using standard genetic techniques. Briefly, the RRN3G-316 plasmid was transformed into the RLY300 strain containing the RRN3G-425 plasmid. Following selection for cells transformed with the RRN3G-316 plasmid, the cells were grown under partially selective conditions so that the RRN3G-425 plasmid was lost. The resulting cells, that contained only the RRN3G-316 plasmid, were grown on 5-fluoroorotic acid (5-FOA) plates to select against the presence of the RRN3G-316 plasmid. No colonies grew on these plates, which demonstrated that the RRN3G-316 plasmid, containing the yeast RRN3 gene, could rescue a yeast strain missing the endogenous yeast Rrn3 protein.

Example 7

Expression of Human RRN3 in Yeast

The human and the yeast RRN3 polypeptides were expressed as polyoma epitope-tagged fusion proteins from the yeast PGK promoter in rrn3$^-$ strain RLY303 (MATa ade2–1 his3–11 leu2–3,112 trp1–1,15 ura3–1 can1–100 RAD5 rrn3Δ::HIS3 [pNOY-TRP1]). Strain RLY303, a Nomura plasmid-dependent rrn3$^-$ strain, was created by transforming strain RLY302 (MATa ade2–1 his3–11 leu2–3, 112 trp1–1,15 ura3–1 can1–100 RADS rrn3Δ::HIS3 [pRRN3G-316]) with pNOY-W (a derivative of pNOY103 (see Nogi et al., *Proc. Natl. Acad. Sci. USA* 88:7026–30 (1991))). pNOY-W expresses the yeast 35S rRNA precursor under the control of the yeast GAL7 promoter. For this experiment, the URA3 gene was disrupted by insertion of the TRP1 gene.

Constructs for expression of polyoma-tagged Rrn3 polypeptides in yeast were generated as follows: a double-stranded oligonucleotide encoding two copies of the polyoma epitope and a single copy of the FLAG tag was inserted into a pRS425 derivative containing the yeast PGK promoter (Lin et al. supra). The coding regions of the yeast RRN3 or human RRN3 cDNA were PCR-amplified and inserted in-frame with the epitope cassette to create yPyWT and PyhRRN3, respectively. All constructs were confirmed by sequencing.

Strain RLY303 is only viable on galactose-containing media because the RRN3 gene is only expressed from the PGK promoter on that media. RLY303 was transformed with either yeast wild-type RRN3 (yPyWT), the human cDNA (PyhRRN3), or the control expression vector and grown under appropriate selection on galactose plates. The resulting transformants (Trp$^+$) were then streaked on CM-glucose plates to monitor RRN3 function, or on CM-galactose plates as a positive control, and were incubated at 25° C., 30° C., or 37° C. When colonies were streaked onto glucose medium to repress transcription from the yeast GAL7 promoter, cells expressing either yeast or human Rrn3 grew at all temperatures tested, while those transformed with the empty expression construct were inviable.

The ability of the human cDNA to complement the Rrn3$^-$ mutation demonstrates that its function in pol I transcription is conserved between yeast and humans and that the region of the human polypeptide encoded by the partial human RRN3 cDNA is sufficient for in vivo activity in yeast. Interestingly, the yeast and human RRN3 genes display distinct conditional phenotypes in the rrn3⁻ background. Cells carrying the yeast gene grow well at 25° C. and 30° C., but show slightly reduced growth at 37° C. In contrast, cells transformed with human RRN3 cDNA grow better than yeast RRN3 transformants at 37° C. and show a pronounced reduction of growth at 25° C. These temperature-dependent growth differences are not observed when the transformed cells are maintained on galactose.

Expression of the human RRN3 cDNA in yeast was verified by Western blot analysis. Briefly, yeast transformants RLY303 containing the yeast wild-type RRN3 (yPyWT), the human RRN3 cDNA (PyhRRN3), or the control expression vector were grown to O.D. 600=2 in 50 ml of galactose medium lacking leucine to select for the polyoma fusion expression constructs. Cells were harvested by centrifugation, washed once with water, once with Yeast Extraction Buffer (YEB: 100 mM HEPES pH 7.9, 20% glycerol, 0.5 M KCl, 5 mM EGTA, 1 mM EDTA) and resuspended in 1.5 pellet volumes of YEB containing 2.5 mM DTT and protease inhibitors, as described by Lin et al. (supra). An equal volume of glass beads was added, and cells were lysed by shaking 4×40 seconds in a FASTPREP® apparatus (Savant). The supernatant was transferred and spun in a microfuge for 20 minutes at 4° C. Fusion proteins were visualized by Western blot analysis using purified anti-polyoma epitope antibodies (Grussenmeyer et al., *Proc. Natl. Acad. Sci. USA* 82:7952–54 (1985)) at a 1/5,000 dilution. The resulting Western blots demonstrated that the human RRN3 cDNA was expressed in RLY303, as evidenced by anti-polyoma epitope binding to a polypeptide of the predicted molecular weight.

Example 8

Mutagenesis of the Yeast and Human RRN3 Genes

To determine if the observed sequence conservation between yeast and human Rrn3 contributes to its function, the effect of an amino acid substitution at leucine 136 on the in vivo activity of the two polypeptides was compared. A temperature-sensitive mutant strain, which has a leucine to proline substitution at position 143 of yeast Rrn3, was used. This strain exhibits reduced growth at 37° C. Because the polypeptide sequence alignment indicates that this residue was conserved in the human Rrn3 polypeptide, a leucine to proline substitution was constructed at the corresponding amino acid position ("L136P") in human RRN3 cDNA by site directed mutagenesis, as follows: PyhL136P was generated by site-directed mutagenesis (Kunkel, *Proc. Natl. Acad. Sci. USA* 82:488–92 (1985)) using oligonucleotide (5'-AACAGTCTGTGCTGATAC AGGATTACCAAGAAAAGCCAA-3'; SEQ ID NO:8) (substitution underlined) to introduce a leucine to proline substitution at amino acid position 136 of human RRN3 (PyhRRN3). The coding regions of the yeast RRN3 gene, the yeast L143P mutant, the human RRN3 cDNA and the human L136P RRN3 mutant were amplified by PCR and inserted in-frame with the pRS425 epitope cassette to create vectors yPyWT, yPyL143P, PyhRRN3 and Pyh136P, respectively. All constructs were confirmed by DNA sequence analysis, and expression was verified by Western blot analysis.

The ability of the wild-type and mutant human polypeptides to complement the rrn3⁻ knockout strain were examined. The temperature-sensitive phenotype of the yeast L143P mutant is observed when cells are streaked to glucose plates or when serial dilutions of wild-type and mutant transformants are compared at 30° C. and 37° C. In contrast, the human Rrn3 L136P mutant was unable to support growth on glucose at either temperature. To confirm that the Rrn3 L136P mutant was stably expressed, lysates were prepared from the transformants and were subjected to Western blot analysis using an antibody directed against the polyoma epitope, as described above. While full-length polypeptide is readily detected in all transformants, the levels of the human L136P mutant are reduced with respect to the human wild-type polypeptide. It is possible that increased expression of the human Rrn3 L136P mutant would result in a conditional phenotype similar to that observed with the yeast Rrn3 L143P mutant. It is clear, however, that the loss of in vivo function of Rrn3 L136P mutant is not solely the result of reduced expression because the human wildtype polypeptide is still capable of rescuing the rrn3⁻ strain when it is expressed at levels comparable to those of hL136P. Therefore, the conserved leucine residue contributes to the in vivo function of both the yeast and human polypeptides.

Example 9

Identification of Other Eukaryotic RRN3 Genes

The yeast Rrn3 polypeptide sequence was used as a reference sequence in a BLAST search (Altschul et al., *Nucl. Acids Res.* 25:3389–402 (1997)) to scan an EST database for other RRN3 genes. Full length homologs were identified in *Schizosaccharomyces pombe* (sp|Q10110), *Caenorhabditis elegans* (sp|P48322), and three paralogs were identified in *Arabidopsis thaliana* (gb|AAD25746, gb|AAC16259, gb|AAC28984). Searching against unfinished genomic sequences reveals a near full length sequence from *Candida albicans* (gnl|Stanford_5476), and a partial sequence from *Drosophila melanogaster* mapping to chromosome 2 region 40D (gb|AC011757).

Rrn3 homologs in other eukaryotes are recognized by their similarity to these sequences. A partial list of Rrn3 EST's from other organisms includes mouse (gb|AA530643), zebra fish (gb|AI816698), *Botrytis cinerea* (emb|AL112233), rice (gb|AA752612), aspen (gb|AI164160), and poplar (gb|AI166768).

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. An isolated nucleic acid selected from the group consisting of
   (a) a nucleic acid that encodes an RRN3 polypeptide having the amino acid sequence set forth in SEQ ID NO:2, and
   (b) the full-length complement of the nucleic acid of (a).

2. The nucleic acid of claim 1, which is cDNA, or RNA.

3. The nucleic acid of claim 1, which has the nucleotide sequence set forth in SEQ ID NO:1, or the full-length complement thereof.

4. An expression construct comprising the following operably linked elements:
   a transcriptional promoter;
   a nucleic acid coding for an RRN3 polypeptide having the amino acid sequence set forth in SEQ ID NO:2; and
   a transcriptional terminator.

5. The expression construct of claim 4, wherein the nucleic acid coding for the RRN3 polypeptide has the nucleotide sequence set forth in SEQ ID NO:1.

* * * * *

SEQUENCE LISTING

<160> NUMBER OF SEQ ID NOS: 8

<210> SEQ ID NO 1
<211> LENGTH: 2068

<212> TYPE: DNA
<213> ORGANISM: Homo sapiens

<400> SEQUENCE: 1

```
acagaggctg tggctggaag gagctgggca tccggcctga ggcgcagcgg tcgcgttagt      60
tcggcccaat ggcggcaccg ctgcttcaca cgcgtttgcc gggagatgcg gccgcttcgt     120
cctctgcagt taagaagctg ggcgcgtcga ggactgggat ttcaaatatg cgtgcattag     180
agaatgactt tttcaattct cccccaagaa aaactgttcg gtttggtgga actgtgacag     240
aagtcttgct gaagtacaaa aagggtgaaa caaatgactt tgagttgttg aagaaccagc     300
tgttagatcc agacataaag gatgaccaga tcatcaactg gctgctagaa ttccgttctt     360
ctatcatgta cttgacaaaa gactttgagc aacttatcag tattatatta agattgcctt     420
ggttgaatag aagtcaaaca gtagtggaag agtatttggc ttttcttggt aatcttgtat     480
cagcacagac tgttttcctc agaccgtgtc tcagcatgat tgcttcccat tttgtgcctc     540
cccgagtgat cattaaggaa ggcgatgtag atgtttcaga ttctgatgat gaagatgata     600
atcttcctgc aaattttgac acatgtcaca gagccttgca ataatagca agatatgtac      660
catcgacacc gtggtttctc atgccaatac tggtggaaaa atttccattt gttcgaaaat     720
cagagagaac actggaatgt tacgttcata acttactaag gattagtgta tattttccaa     780
ccttgaggca tgaaattctg gagcttatta ttgaaaaact actcaagttg gatgtgaatg     840
catcccggca gggtattgaa gatgctgaag aaacagcaac tcaaacttgt ggtgggacag     900
attccacgga aggattgttt aatatggatg aagatgaaga aactgaacat gaaacaaagg     960
ctggtcctga acggctcgac cagatggtgc atcctgtagc cgagcgcctg gacatcctga    1020
tgtctttggt tttgtcctac atgaaggatg tctgctatgt agatggtaag gttgataacg    1080
gcaaaacaaa ggatctatat cgcgacctga taaacatctt tgacaaactc ctgttgccca    1140
cccatgcctc ctgccatgta cagttttcca tgttttacct ctgtagtttc aaattgggat    1200
tcgcagaggc attttggaa catctctgga aaaaattgca ggacccaagt aatcctgcca    1260
tcatcaggca ggctgctgga aattatattg gaagcttttt ggcaagagct aaatttattc    1320
ctcttattac tgtaaaatca tgcctagatc ttttggttaa ctggctgcac atataccttaa    1380
ataaccagga ttcgggaaca aaggcattct gcgatgttgc tctccatgga ccatttact     1440
cagcctgcca agctgtgttc tacacctttg ttttttagaca caagcagctt ttgagcggaa    1500
acctgaaaga aggtttgcag tatcttcaga gtctgaattt tgagcggata gtgatgagcc    1560
agctaaatcc cctgaagatt tgcctgccct cagtggttaa cttttttgct gcaatcacaa    1620
ataagtacca gctcgtcttc tgctacacca tcattgagag gaacaatcgc cagatgctgc    1680
cagtcattag gagtaccgct ggaggagact cagtgcagat ctgcacaaac ccgctggaca    1740
ccttcttccc ctttgatccc tgtgtgctga agaggtcaaa gaaattcatt gatcctattt    1800
atcaggtatg ggaagacatg agtgctgaag agctacagga gttcaagaaa cccatgaaaa    1860
aggacatagt ggaagatgaa gatgatgact ttctgaaagg cgaagtgccc cagaatgata    1920
ccgtgattgg gatcacacca agctcctttg acacgcattt ccgaagtcct tcaagtagtg    1980
tgggctcccc acccgtgttg tacatgcaac ccagtcccct ctgacggcag aaatttgtga    2040
ctgagatgtg acatttggga ttcccccat                                       2068
```

<210> SEQ ID NO 2
<211> LENGTH: 651
<212> TYPE: PRT
<213> ORGANISM: Homo sapiens

<400> SEQUENCE: 2

```
Met Ala Ala Pro Leu Leu His Thr Arg Leu Pro Gly Asp Ala Ala
  1               5                  10                  15
Ser Ser Ser Ala Val Lys Lys Leu Gly Ala Ser Arg Thr Gly Ile Ser
            20                  25                  30
Asn Met Arg Ala Leu Glu Asn Asp Phe Phe Asn Ser Pro Pro Arg Lys
        35                  40                  45
Thr Val Arg Phe Gly Gly Thr Val Thr Glu Val Leu Leu Lys Tyr Lys
    50                  55                  60
Lys Gly Glu Thr Asn Asp Phe Glu Leu Leu Lys Asn Gln Leu Leu Asp
 65                  70                  75                  80
Pro Asp Ile Lys Asp Asp Gln Ile Ile Asn Trp Leu Leu Glu Phe Arg
                85                  90                  95
Ser Ser Ile Met Tyr Leu Thr Lys Asp Phe Glu Gln Leu Ile Ser Ile
            100                 105                 110
Ile Leu Arg Leu Pro Trp Leu Asn Arg Ser Gln Thr Val Val Glu Glu
        115                 120                 125
Tyr Leu Ala Phe Leu Gly Asn Leu Val Ser Ala Gln Thr Val Phe Leu
    130                 135                 140
Arg Pro Cys Leu Ser Met Ile Ala Ser His Phe Val Pro Pro Arg Val
145                 150                 155                 160
Ile Ile Lys Glu Gly Asp Val Asp Val Ser Asp Ser Asp Glu Asp
                165                 170                 175
Asp Asn Leu Pro Ala Asn Phe Asp Thr Cys His Arg Ala Leu Gln Ile
            180                 185                 190
Ile Ala Arg Tyr Val Pro Ser Thr Pro Trp Phe Leu Met Pro Ile Leu
        195                 200                 205
Val Glu Lys Phe Pro Phe Val Arg Lys Ser Glu Arg Thr Leu Glu Cys
    210                 215                 220
Tyr Val His Asn Leu Leu Arg Ile Ser Val Tyr Phe Pro Thr Leu Arg
225                 230                 235                 240
His Glu Ile Leu Glu Leu Ile Ile Glu Lys Leu Leu Lys Leu Asp Val
                245                 250                 255
Asn Ala Ser Arg Gln Gly Ile Glu Asp Ala Glu Glu Thr Ala Thr Gln
            260                 265                 270
Thr Cys Gly Gly Thr Asp Ser Thr Glu Gly Leu Phe Asn Met Asp Glu
        275                 280                 285
Asp Glu Glu Thr Glu His Glu Thr Lys Ala Gly Pro Glu Arg Leu Asp
    290                 295                 300
Gln Met Val His Pro Val Ala Glu Arg Leu Asp Ile Leu Met Ser Leu
305                 310                 315                 320
Val Leu Ser Tyr Met Lys Asp Val Cys Tyr Val Asp Gly Lys Val Asp
                325                 330                 335
Asn Gly Lys Thr Lys Asp Leu Tyr Arg Asp Leu Ile Asn Ile Phe Asp
            340                 345                 350
Lys Leu Leu Leu Pro Thr His Ala Ser Cys His Val Gln Phe Phe Met
        355                 360                 365
Phe Tyr Leu Cys Ser Phe Lys Leu Gly Phe Ala Glu Ala Phe Leu Glu
    370                 375                 380
His Leu Trp Lys Lys Leu Gln Asp Pro Ser Asn Pro Ala Ile Ile Arg
385                 390                 395                 400
Gln Ala Ala Gly Asn Tyr Ile Gly Ser Phe Leu Ala Arg Ala Lys Phe
                405                 410                 415
Ile Pro Leu Ile Thr Val Lys Ser Cys Leu Asp Leu Leu Val Asn Trp
```

```
                420             425             430
Leu His Ile Tyr Leu Asn Asn Gln Asp Ser Gly Thr Lys Ala Phe Cys
            435                 440                 445

Asp Val Ala Leu His Gly Pro Phe Tyr Ser Ala Cys Gln Ala Val Phe
    450                 455                 460

Tyr Thr Phe Val Phe Arg His Lys Gln Leu Leu Ser Gly Asn Leu Lys
465                 470                 475                 480

Glu Gly Leu Gln Tyr Leu Gln Ser Leu Asn Phe Glu Arg Ile Val Met
                485                 490                 495

Ser Gln Leu Asn Pro Leu Lys Ile Cys Leu Pro Ser Val Val Asn Phe
            500                 505                 510

Phe Ala Ala Ile Thr Asn Lys Tyr Gln Leu Val Phe Cys Tyr Thr Ile
            515                 520                 525

Ile Glu Arg Asn Asn Arg Gln Met Leu Pro Val Ile Arg Ser Thr Ala
            530                 535                 540

Gly Gly Asp Ser Val Gln Ile Cys Thr Asn Pro Leu Asp Thr Phe Phe
545                 550                 555                 560

Pro Phe Asp Pro Cys Val Leu Lys Arg Ser Lys Lys Phe Ile Asp Pro
                565                 570                 575

Ile Tyr Gln Val Trp Glu Asp Met Ser Ala Glu Glu Leu Gln Glu Phe
                580                 585                 590

Lys Lys Pro Met Lys Lys Asp Ile Val Glu Asp Glu Asp Asp Asp Phe
                595                 600                 605

Leu Lys Gly Glu Val Pro Gln Asn Asp Thr Val Ile Gly Ile Thr Pro
            610                 615                 620

Ser Ser Phe Asp Thr His Phe Arg Ser Pro Ser Ser Val Gly Ser
625                 630                 635                 640

Pro Pro Val Leu Tyr Met Gln Pro Ser Pro Leu
                645                 650

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 3
tgattgcagc aaaaaagtta accactga                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 4
ctatatcgcg acctgataaa catctttg                                          28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 5
caaagatgtt tatcaggtcg cgatatag                                          28
```

```
<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 6
ggaagctttt tggcaagagc taaatttatt cctc                              34

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: PCR Primer

<400> SEQUENCE: 7
gcggatcctc attcagcact catgtcttcc catacctgat a                      41

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 8
aacagtctgt gctgatacag gattaccaag aaaagccaa                         39
```